(12) United States Patent
Ho

(10) Patent No.: US 7,189,360 B1
(45) Date of Patent: Mar. 13, 2007

(54) CIRCULAR CHEMIRESISTORS FOR MICROCHEMICAL SENSORS

(75) Inventor: Clifford K. Ho, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 693 days.

(21) Appl. No.: 10/349,772

(22) Filed: Jan. 23, 2003

Related U.S. Application Data

(60) Provisional application No. 60/351,535, filed on Jan. 24, 2002.

(51) Int. Cl.
```
B32B 5/02       (2006.01)
B32B 27/04      (2006.01)
B32B 27/12      (2006.01)
G01N 15/06      (2006.01)
G01N 25/18      (2006.01)
```
(52) U.S. Cl. .................. 422/82.02; 422/50; 422/68.1; 422/83; 422/98; 422/82.01; 436/149; 29/592.1; 73/1.01; 73/1.02; 73/23.2
(58) Field of Classification Search ................. 422/50, 422/68.1, 83, 98, 82.01, 82.02; 436/149; 29/592.1; 73/1.01, 1.02, 23.2
See application file for complete search history.

(56) References Cited

U.S. PATENT DOCUMENTS

| | | | | |
|---|---|---|---|---|
| 4,636,767 A | * | 1/1987 | Barger et al. | 338/34 |
| 4,886,625 A | * | 12/1989 | Albarella et al. | 252/500 |
| 4,992,244 A | * | 2/1991 | Grate | 422/98 |
| 5,045,285 A | * | 9/1991 | Kolesar, Jr. | 422/98 |
| 5,512,882 A | * | 4/1996 | Stetter et al. | 340/632 |
| 5,571,401 A | * | 11/1996 | Lewis et al. | 205/787 |
| 5,951,846 A | | 9/1999 | Lewis et al. | 205/787 |
| 6,746,960 B2 | * | 6/2004 | Goodman | 438/689 |

OTHER PUBLICATIONS

Ho and Hughes, "In-Situ Chemiresistor Sensor Package for Real-Time Detection of Volatile Organic Compounds in Soil and Groundwater", Sensors 2002, 2, 23-24.

Hughes, Patel, and Manginell, "A MEMS Based Hybrid Preconcentrator/Chemiresistor Chemical Sensor", 198th ECS Meeting, Phoenix, AZ, Proceedings of the Fifth Symposium on Microfabricated Systems and MEMS, vol. 2001-19, Oct. 2000, pp. 142-150.

Hughes, et al., "Integrated Chemiresistor Array for Small Sensor Platforms", SPIE Proceedings paper 4038-62, AeroSense 2000, Apr. 24-28, 2000, vol. 4038, p. 519.

(Continued)

*Primary Examiner*—Brian Sines
(74) *Attorney, Agent, or Firm*—Robert D. Watson

(57) ABSTRACT

A circular chemiresistor for use in microchemical sensors. A pair of electrodes is fabricated on an electrically insulating substrate. The pattern of electrodes is arranged in a circle-filling geometry, such as a concentric, dual-track spiral design, or a circular interdigitated design. A drop of a chemically sensitive polymer (i.e., chemiresistive ink) is deposited on the insulating substrate on the electrodes, which spreads out into a thin, circular disk contacting the pair of electrodes. This circularly-shaped electrode geometry maximizes the contact area between the pair of electrodes and the polymer deposit, which provides a lower and more stable baseline resistance than with linear-trace designs. The circularly-shaped electrode pattern also serves to minimize batch-to-batch variations in the baseline resistance due to non-uniform distributions of conductive particles in the chemiresistive polymer film.

23 Claims, 33 Drawing Sheets

OTHER PUBLICATIONS

Hughes, Manginell, and Kottenstette, "Chemical Sensing with an Integrated Preconcentrator/Chemiresistor Array", Proc. Of Symposium on Chemical and Biological Sensors and Analytical Methods II, ECS Meeting, San Francisco, CA, vol. 2001-18, Sep. 2001, p. 348.

Hughes, et al., "Apparatus for Sensing Volatile Organic Chemicals in Fluids", U.S. Appl. No. 09/974,327, filed Oct. 9, 2001.

Ballantine, et al., Acoustic Wave Sensors, Academic Press, San Diego, pp. 347-355.

* cited by examiner

Sec. A-A

Sec. A-A

Sec. A-A

CIRCULAR CHEMIRESISTORS FOR MICROCHEMICAL SENSORS

CROSS-REFERENCE TO RELATED APPLICATIONS

This application claims the benefit of U.S. Provisional patent application Ser. No. 60/351,535 "Novel Designs and Deposition Methods for Polymer-Based Microchemical Sensors", by Clifford K. Ho, filed Jan. 24, 2002, which is incorporated herein by reference. This application is related to co-pending application Ser. No. 09/974,327, "Apparatus for Sensing Volatile Organic Chemicals in Fluids", by Hughes, et al, which is incorporated herein by reference. This application is related to co-pending application, "Confined Cavity Chemiresistors for Microchemical Sensors", by Clifford K. Ho, filed Jan. 23, 2003. This application is related to co-pending application, "Multi-Pin Chemiresistors for Microchemical Sensors", by Clifford K. Ho, filed Jan. 23, 2003.

FEDERALLY SPONSORED RESEARCH

The United States Government has rights in this invention pursuant to Department of Energy Contract No. DE-AC04-94AL85000 with Sandia Corporation.

BACKGROUND OF THE INVENTION

This invention relates generally to the use of polymer-based chemiresistor sensing elements in microchemical sensors that are capable of detecting small concentrations of vapors emitted by volatile organic compounds (VOC) or other volatile compounds (VC).

Polymer-based vapor absorption type sensors are attractive choices for use in VOC monitoring devices that are used, for example, for environmental monitoring in the vadose zone. Examples of these microchemical sensors include conductometric sensors such as chemiresistors, surface or thickness-shear mode acoustic wave (SAW) mass sensors, flexural plate wave mass sensors, and MEMS microcantilever mass sensors. Chemiresistors are a particularly simple and inexpensive type of chemical sensor whose electrical resistance changes when exposed to certain chemical vapors. Micro-sized chemiresistor sensors are relatively easy to fabricate using well-known semiconductor fabrication techniques; can be made very small (<100 square microns); can operate at ambient temperatures; are passive devices (no pumps or valves are needed); are relatively inexpensive; and their resistance change can be read-out by a simple, low power (and low current) circuit that measures DC resistance. This feature allows the use of long electrical cables, which allows the resistance measurement unit and data logging equipment to be remotely located. Also, chemiresistors are more resistant to chemical poisoning than other types of sensors (e.g., catalytic sensors).

A common type of chemiresistor consists of a chemically sensitive, electrically insulating, organic, soluble polymer matrix that is loaded with a large volume (e.g., 20–40%) of electrically conductive metallic (e.g., gold, silver) or carbon/graphite particles to form a composite material having continuous networks of electrically conductive pathways throughout the polymer matrix (i.e., host). To fabricate a chemiresistor, the polymer is dissolved with a solvent (e.g., water, chlorobenzene, or chloroform) and sub-micron diameter carbon, silver, or gold particles (e.g., 20–30 nanometers) are added to make a "chemiresistive ink" (carbon particles are most commonly used). Typically, 0.1 g of solids (polymer plus carbon particles) are dissolved in 5 mL of solvent. Acoustic vibration using a pulsed, point ultrasonic source can be used to uniformly disperse the particles. A non-ionic surfactant can be added to this mixture to chemically bond to the electrically conducting particles and thereby form steric barriers, which prevent undesirable aggregation or agglomeration of these particles. Spin casting can produce films from 200–400 nm thick, while pipetted films are generally thicker (e.g., 1–10 microns) and less uniform in thickness than the spun films. A filter (e.g., a 5 micron pore size filter) can be used to screen the ink and remove any large agglomerations of the conductive particles prior to deposition. Then, the resulting ink is deposited as a thin film (typically onto an insulating substrate contacting two or more spaced-apart electrodes (i.e. resistor leads), and then dried by evaporation.

When chemical vapors of solvents, toxic chemicals, explosives, or VOCs come into contact with the chemically sensitive polymer composite, the polymer matrix absorbs the vapor(s) and swells. The swelling spreads apart the embedded conductive particles, breaking some of the conductive pathways. This increases the electrical resistance across the two or more electrodes by an amount that is easily measured and recorded. The amount of swelling in steady state, and, hence, the steady-state resistance change, can be uniquely related to the concentration of the chemical vapor(s) in equilibrium with the chemiresistor film. The resistance response is generally linear with increasing vapor concentration, but can become non-linear at high solvent concentrations when the percolation threshold of the polymer composite is reached (i.e., 20–40% swelling). The swelling process is generally reversible; hence the polymer matrix will shrink when the source of chemical vapor is removed (although some hysteresis can occur).

The polymer matrix used in chemiresistors can absorb multiple solvents having similar solubility parameters. Since it is unlikely that any specific polymer will be sensitive to only one particular VOC, an array of multiple chemiresistors containing a variety of polymer hosts is generally needed to provide accurate discrimination among multiple, interfering vapors (including water vapor).

Multiple chemiresistors have been fabricated side-by-side on a common substrate, such as a silicon wafer, where each chemiresistor has a different thin film polymer matrix selected for high sensitivity to a particular VOC of interest. The more unknown VOCs there are, the greater the number of different polymers is needed to provide adequate discrimination. Hence, a fast and accurate identification technique is needed that can distinguish between multiple types of solvents (polar and non-polar), for both pure compounds and mixtures, over a wide range of concentrations, and in the presence of water vapor.

A common and obvious source of interfering vapors is water vapor (i.e., relative humidity) in the ambient environment. Water vapor affects the relative sensitivity of certain polymers to solvent vapors, and affects the patterns of responses obtained from arrays containing those polymers. A microchemical sensor that is capable of identifying the maximum number of possible analytes should have multiple chemiresistor elements that are as chemically varied as possible, with at least one chemiresistor having significant sensitivity to water vapor.

Arrays of chemiresistor sensing elements fabricated on a single substrate have been successfully used to detect a wide variety of VOCs, including aromatic hydrocarbons (e.g., benzene), chlorinated solvents (e.g., trichloroethylene (TCE), carbon tetrachloride, aliphatic hydrocarbons (e.g., hexane, iso-octane), alcohols, and ketones (e.g., acetone)). Other VOCs of interest to groundwater protection include methyl tert-butyl ether (MTBE), other gasoline additives, toluene, and xylene.

Chemiresistor and surface-acoustic wave (SAW) sensors use chemically sensitive polymer composite films to absorb/adsorb analytes of interest, which produces changes in the sensor's characteristics (e.g., resistance, resonance vibration frequency, etc.). A variety of solvent casting techniques have been used to deposit the polymeric coatings on these sensors, including: spray coating, spin casting, dip coating, painting with small brushes or Q-tips, dabbing, and syringe deposition. In solvent casting, the polymer with particulate additive is dissolved/suspended in a solvent to form a solution, which is then deposited on a substrate and allowed to dry, whereby the solvent evaporates to leave the desired coating material.

The repeatability, reliability, and performance of these microchemical sensors depend on the volume, area, electrode contact area, and composition (including uniformity of composition) of the deposited chemically sensitive polymer composite. Unfortunately, these parameters are not well controlled using current methods of solvent casting. Many of the methods described above rely on gravity-driven or pressure-driven means to deposit dissolved polymers onto a solid surface. Tools that are used in these methods require that the solution be placed inside a machine or tool that squirts or drips a microdrop of liquid (e.g., micrograms) onto the desired surface. Precise placement and volume control is challenging. In the fabrication of chemiresistor-type microchemical sensors (where conductive particles are dispersed within a polymer matrix), clogging can occur if the solvent dries while the chemiresistive ink is introduced or stored in the machine, or while the ink is being ejected from the machine. This creates unacceptable variability in the conductive particle/polymer ratio, which directly affects the repeatability and performance of chemiresistors; as well as reducing the production yields (e.g., yields greater than 30% are difficult to achieve due to nozzle clogging with automatic machines). Filters can be used to help reduce clogging, but then the filters get clogged.

Manual techniques, such as hand painting, brushing, dabbing, etc. have been used, but suffer from poor reproducibility and imprecise placement. Micropipettes (i.e., microcaps) have been used to manually deposit microdrops with better volume control and accuracy than by hand brushing. Microcaps having volumes ranging from 1–100 microliters, typically 10–25 microliters, and diameters less than 1 millimeter have been used to deposit drops having a volume less then 1 microliter. However, the accuracy of placement and control of amount of material deposited, is highly dependent on the skill and experience of the technician. Hence, it is not uncommon for the baseline electrical resistance of these manually placed polymer composite films to vary by factors of 2–3, which is clearly unacceptable for commercial manufacture.

FIG. 1A shows a photomicrograph of an example of a microchemical sensor with four chemiresistors, using a linear electrode pattern and four different linear polymer films. The four different polymer films are poly(n-vinyl pyrrolidone) PNVP; poly(vinyl alcohol) PVA; poly(ethylene-vinyl acetate) PEVA; and poly(isobutylene) PIB, and a linear electrode pattern. The microsensor chip is packaged in a 16-pin dual-inline-package (DIP) with outer dimension of about 3 cm by 0.7 cm. In this example, an Asymtek Century Series C-702 Automated Dispensing Unit was used to deposit the conductive inks, with a 27 gauge, ½" long needle and the 740V Low Viscosity attachment, at a rate of 1.5 inches per second, resulting in a linear polymer film approximately 500 microns wide by 2300 microns long. The samples were dried at room temperature under ambient conditions.

The electrode patterns (i.e., resistor leads) for the four chemiresistors, the two heater strips, and the temperature sensor were made of platinum and titanium created using standard photolithographic techniques on a silicon wafer with a 200 nm thick insulating silicon nitride layer. The platinum (1000 A) on titanium (200 A) features were deposited by evaporation. The electrode patterns comprise four parallel conductors (i.e., metallized traces). This electrode layout provides a four-point resistance measurement, which helps to minimize contact resistance effects. The final dimensions of the deposited film (e.g., thickness, width, length, uniformity etc.) are highly dependent on the deposition rate, wetting characteristics, and viscosity of each ink, among other factors.

FIG. 1B shows a photomicrograph of another example of a microchemical sensor with four chemiresistors, using a linear electrode pattern and four different linear polymer films. In both FIGS. 1A and 1B, the edges and composition of the four different polymer composite films are non-uniform and irregular, despite being deposited by the Asymtek Automated Dispensing Unit. Also, some of the deposited films have spread wider, or more irregularly, than others (e.g., PEVA), likely due to differences in the wetting and drying characteristics of the solvent; combined with the observation that the liquid inks were deposited on a flat substrate with no raised borders or surface features to confine the perimeter of the blob/drop of ink to any particular shape or geometry.

FIGS. 2A and 2B show photomicrographs of other examples of a microchemical sensor with four chemiresistors, using a linear electrode pattern and four different circular polymer films. Here, the polymer composite films were deposited manually as drops using a micropipette technique. The PECH and PIB polymers were dissolved in chloroform; the PNVP was dissolved in water, and the PEVA was dissolved in TCE. However, despite the use of a micropipette tool to deposit nominally "circular" films having a diameter of approximately 1.5–2.5 mm, the edges and composition of the deposited films are also irregular and non-uniform. In some of the dried films, a dark ring can be seen around the outer perimeter of the drop. This is likely caused by a higher concentration of the black carbon particles that have migrated to the outside during deposition and drying, due to the "coffee stain" effect.

Additionally, a large amount of excess material has been deposited on either side of the four parallel electrodes, which causes an unnecessary waste of material. Also, the overall pattern of electrode traces on the substrate (i.e., silicon die) is not particularly compact; since about 50% of the electrode's length is not covered by the chemically sensitive film. Also, the two polymer films on the outside are located closer to the heating element, and might be hotter than the two inside films that are located farther away.

Good adhesion of the polymer composite film to the substrate and the electrodes covered by the film is necessary to make a chemiresistor with good reliability and reproducibility, as well as to minimize batch-to-batch variations and to maximize manufacturing yield. Any partial detachment of the film from the electrodes can create an artificial rise in the resistance reading (i.e., by increasing the contact resistance), which could be incorrectly interpreted as an exposure to VOC vapors (i.e., false positive).

The surfaces of the polymer film in contact with the two or more electrodes are defined as the "electrode contact area". The ratio of the polymer film's area divided by the total electrode contact area is defined as the "contact area ratio", which can range from 0 (no contact) to 1 (100% contact). In FIG. 1, and more so in FIG. 2, it can be seen that a large fraction of the polymer film is not in contact with the electrodes. The contact area ratios for the chemiresistors shown in FIG. 2 range from about 15–30%. The lower the contact area ratio is, the greater the sensitivity of the chemiresistor will be to errors caused by any detachment of the polymer matrix from the electrodes. A design that maximizes the contact area ratio will minimize any errors caused by film detachment, thereby improving the stability and reliability of the chemiresistor. A design having a large contact area ratio will also be less sensitive to errors caused by a non-uniform distribution of the conductive particles embedded in the polymer matrix.

Given a fixed area of polymer film, an electrode layout having a larger contact area ratio will have a lower electrical resistance than a design having a smaller contact area ratio.

U.S. Pat. No. 5,951,846 to Lewis and Freund, Sensor Arrays for Detecting Analytes in Fluids, illustrates an interdigitated array of linear electrodes covered by a conducting polymer film having an ideal, perfectly rectangular shape (See Lewis and Freund, FIGS. 1A-1 and FIGS. 4A-1). Lewis and Freund, however, do not discuss the practical problems of obtaining reproducible and reliable performance, with high manufacturing yields, when depositing realistic polymer composite films having less-than-ideal shapes, thickness variations, and non-uniform composition, etc.

The distribution of conductive particles (e.g., carbon) within a polymer film can be non-uniform if the particles have not been well mixed, or if large clumps or colloids of particles form during deposition and drying. FIG. 3A shows a plan view of a first example of a chemiresistor comprising a circular polymer composite film contacting a pair of linear electrodes, with clusters of agglomerated carbon particles non-uniformly distributed near the center of the film. FIG. 3B shows a plan view of a second example of a chemiresistor comprising a circular polymer composite film contacting a pair of linear electrodes, with clusters of agglomerated carbon particles distributed non-uniformly around the outer perimeter of the film.

Even though the chemiresistor films in FIGS. 3A and 3B have approximately the same number of carbon particle clusters, the distribution of the clusters is quite different. Since the linear electrode pattern contacts only a small area near the center of the film, it is clear that the total resistance of the chemiresistor in FIG. 3A will be quite different (i.e., lower) than that of FIG. 3B, due to the vastly different distributions of clustered carbon particles.

Some solutions to this problem are to screen out the large clusters of carbon particles before deposition using a filter, or to prevent their agglomeration by using ultrasonic vibration to sonify and disperse the particles during deposition and/or drying, or to coat the particles with a anti-steric material that inhibits agglomeration. Another approach is the increase the total contact area of the electrodes in contact with the polymer film, so as to minimize any deviations in the total resistance due to non-uniform distributions of the conductive particles. In this way the electrodes sample a larger volume of the film and effectively smear out any non-uniform distributions.

Never the less, a need remains for improved deposition methods and novel designs for chemiresistor type microchemical sensors that have better repeatability, reliability and performance, in a more compact footprint, and with reduced manufacturing costs.

Against this background, the present invention was developed.

SUMMARY OF THE INVENTION

The present invention relates to a circular chemiresistor for use in microchemical sensors. A pair of electrodes is fabricated on an electrically insulating substrate. The pattern of electrodes is arranged in a circle-filling geometry, such as a concentric, dual-track spiral design, or a circular interdigitated design. A drop of a chemically sensitive polymer (i.e., chemiresistive ink) is deposited on the insulating substrate on top of the pair of electrodes, which spreads out into a thin, circular disk contacting the pair electrodes. This circularly-shaped electrode geometry maximizes the contact area between the pair of electrodes and the polymer deposit, which provides a lower and more stable baseline resistance than with linear-trace designs. The circularly shaped electrode pattern also serves to minimize batch-to-batch variations in the baseline resistance due to non-uniform distributions of conductive particles in the chemiresistive polymer film.

BRIEF DESCRIPTION OF THE DRAWINGS

The accompanying drawings, which are incorporated in and form part of the specification, illustrate various examples of the present invention and, together with the detailed description, serve to explain the principles of the invention.

DETAILED DESCRIPTION OF THE INVENTION

The words "vapor" and "gas" are used interchangeably herein. Similarly, the acronym VOC, which stands for Volatile Organic Compound, is intended herein to also encompass all inorganic volatile compounds (VCs), other solvents, volatile toxic chemicals, volatile explosives, and organic compounds even having low volatility.

The words "polymer film", "polymer coating", "chemically sensitive polymer film", "polymer composite", "chemically sensitive polymer deposit", "polymer deposit", unless otherwise defined, all refer to the disc of chemiresistive ink after it has been deposited on a substrate and dried.

Figure 1A:
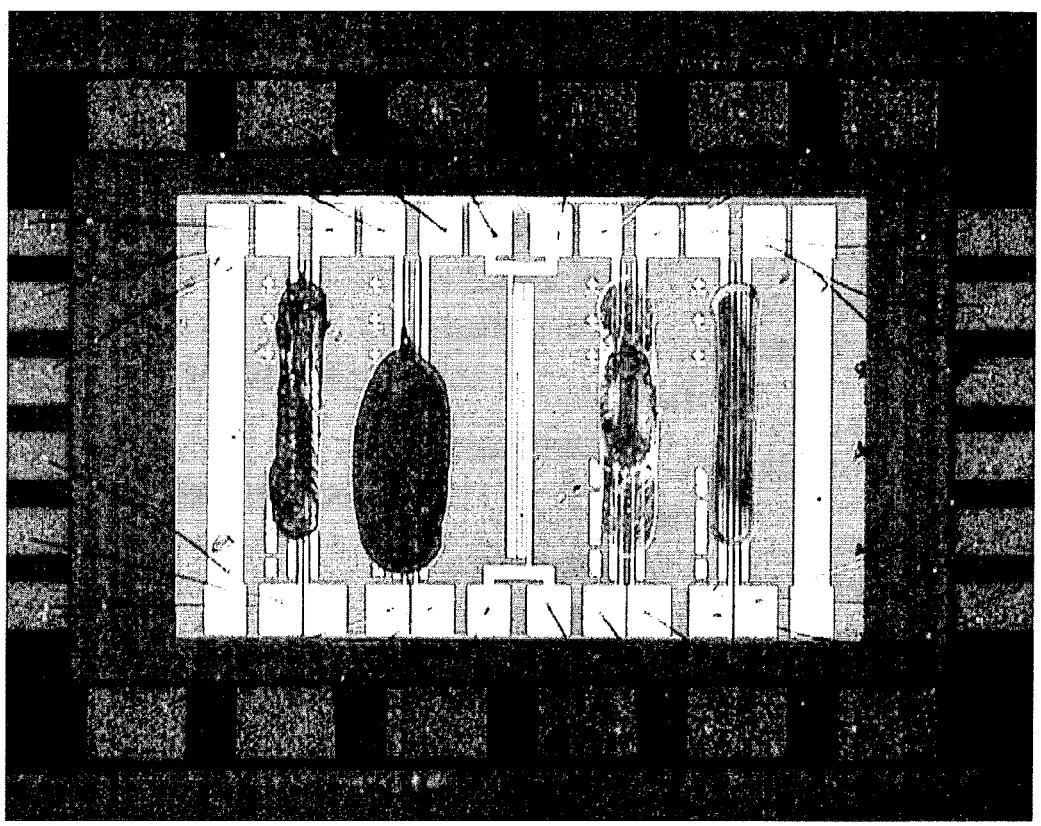
FIG. 1A shows a photomicrograph of an example of a microchemical sensor with four chemiresistors, using a linear electrode pattern and four different linear polymer films.
Figure 1B:
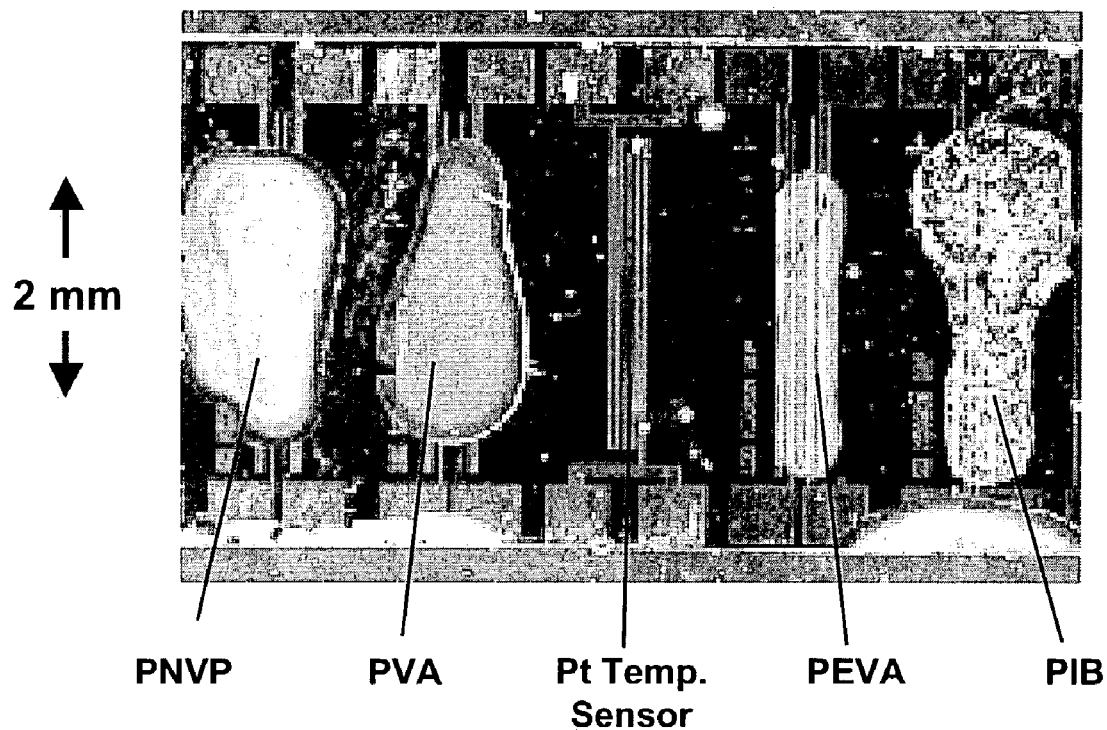
FIG. 1B shows a photomicrograph of an example of a microchemical sensor with four chemiresistors, using a linear electrode pattern and four different linear polymer films.
Figure 2A:
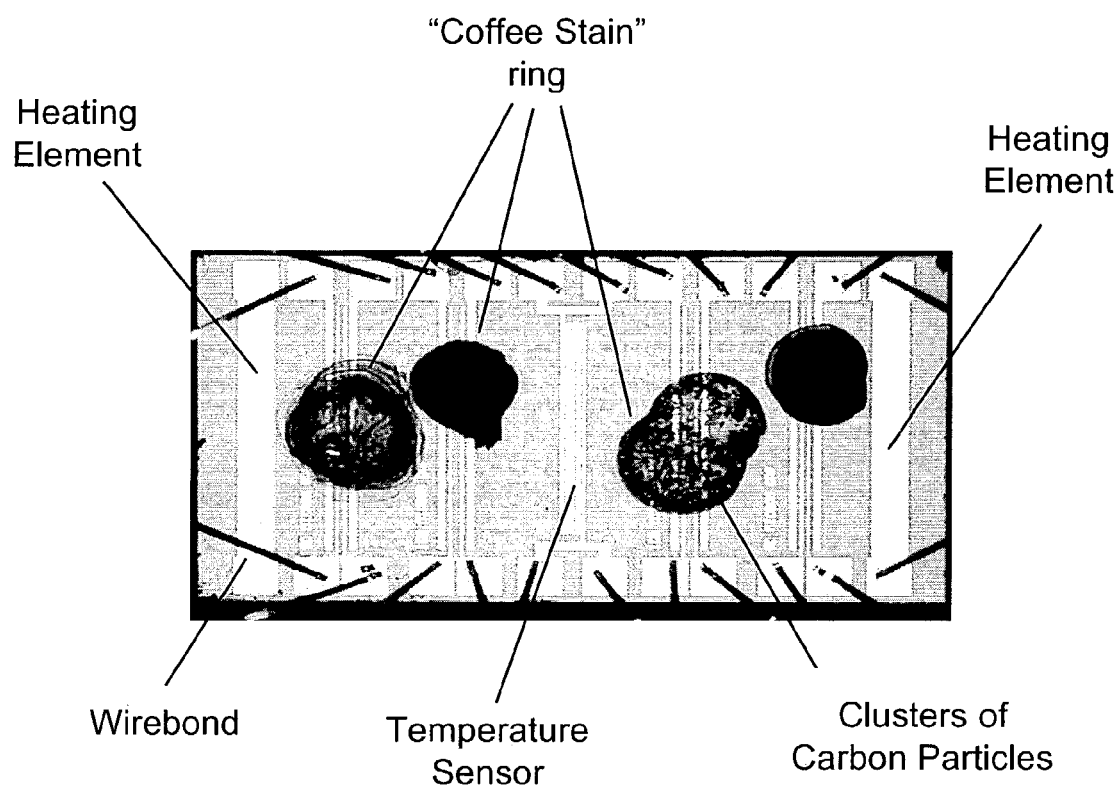
FIG. 2A shows a-photomicrograph of another example of a microchemical sensor with four chemiresistors, using a linear electrode pattern and four different circular polymer films.
Figure 2B:
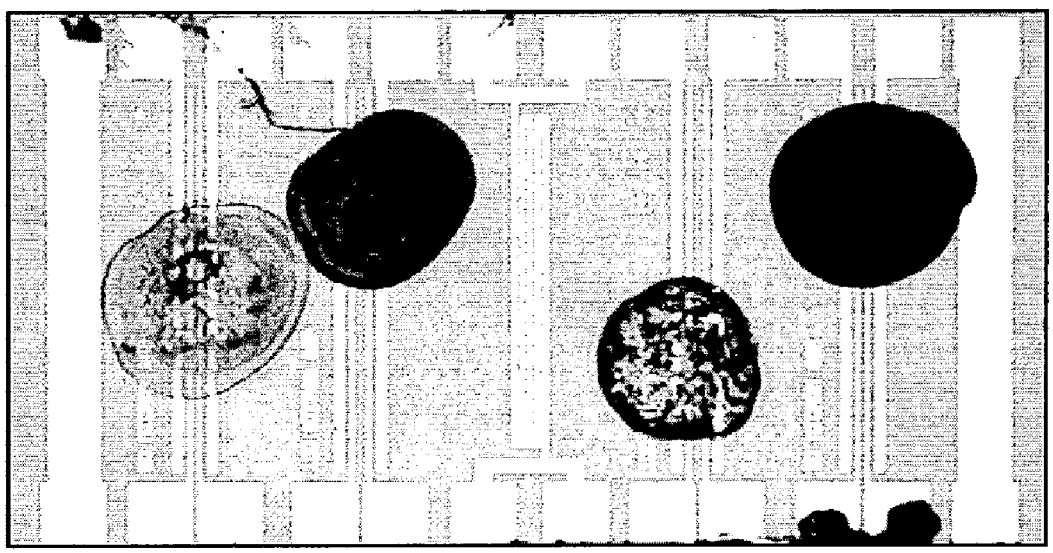
FIG. 2B shows a photomicrograph of another example of a microchemical sensor with four chemiresistors, using a linear electrode pattern and four different circular polymer films.
Figure 3A:
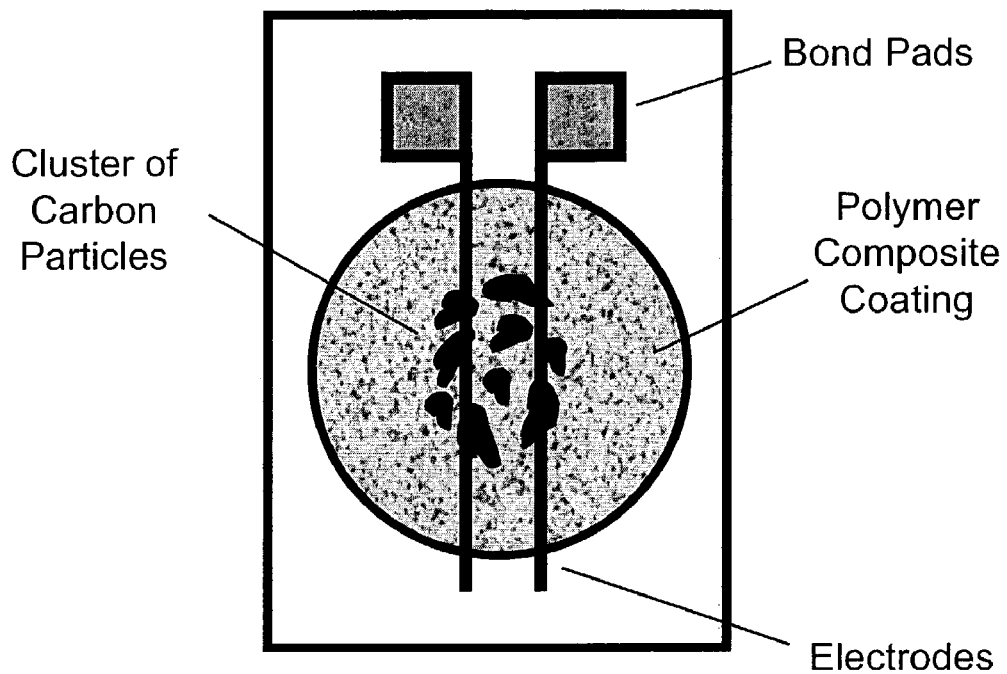
FIG. 3A shows a plan view of a first example of a chemiresistor comprising a circular polymer composite film contacting a pair of linear electrodes, with clusters of agglomerated carbon particles non-uniformly distributed near the center of the film.
Figure 3B:
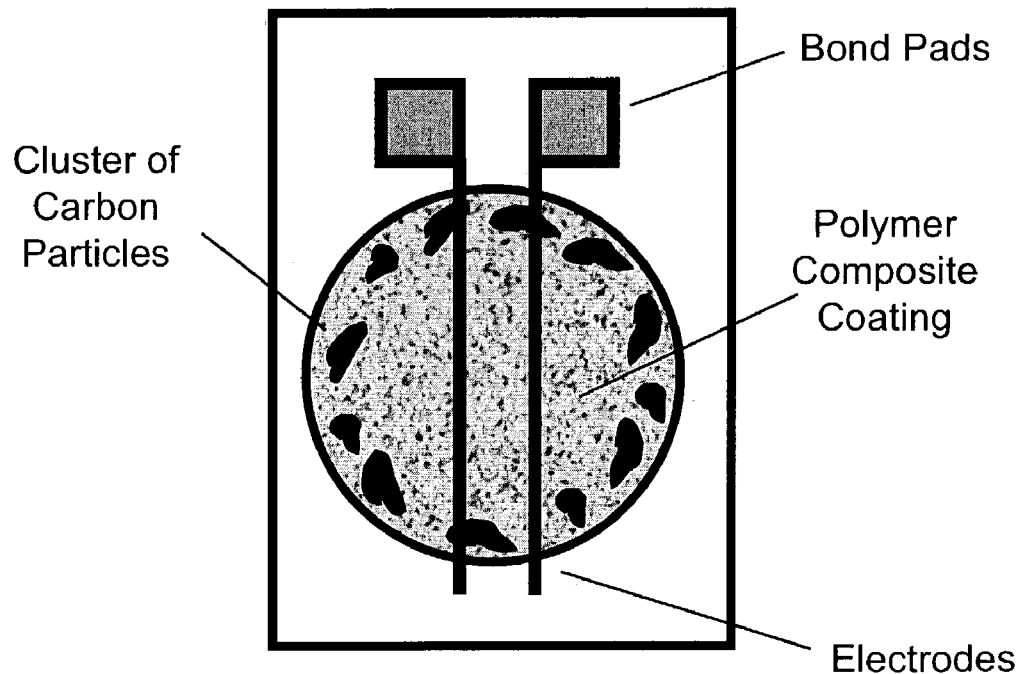
FIG. 3B shows a plan view of a second example of a chemiresistor comprising a circular polymer composite film contacting a pair of linear electrodes, with clusters of agglomerated carbon particles distributed non-uniformly around the outer perimeter of the film.
Figure 4A:
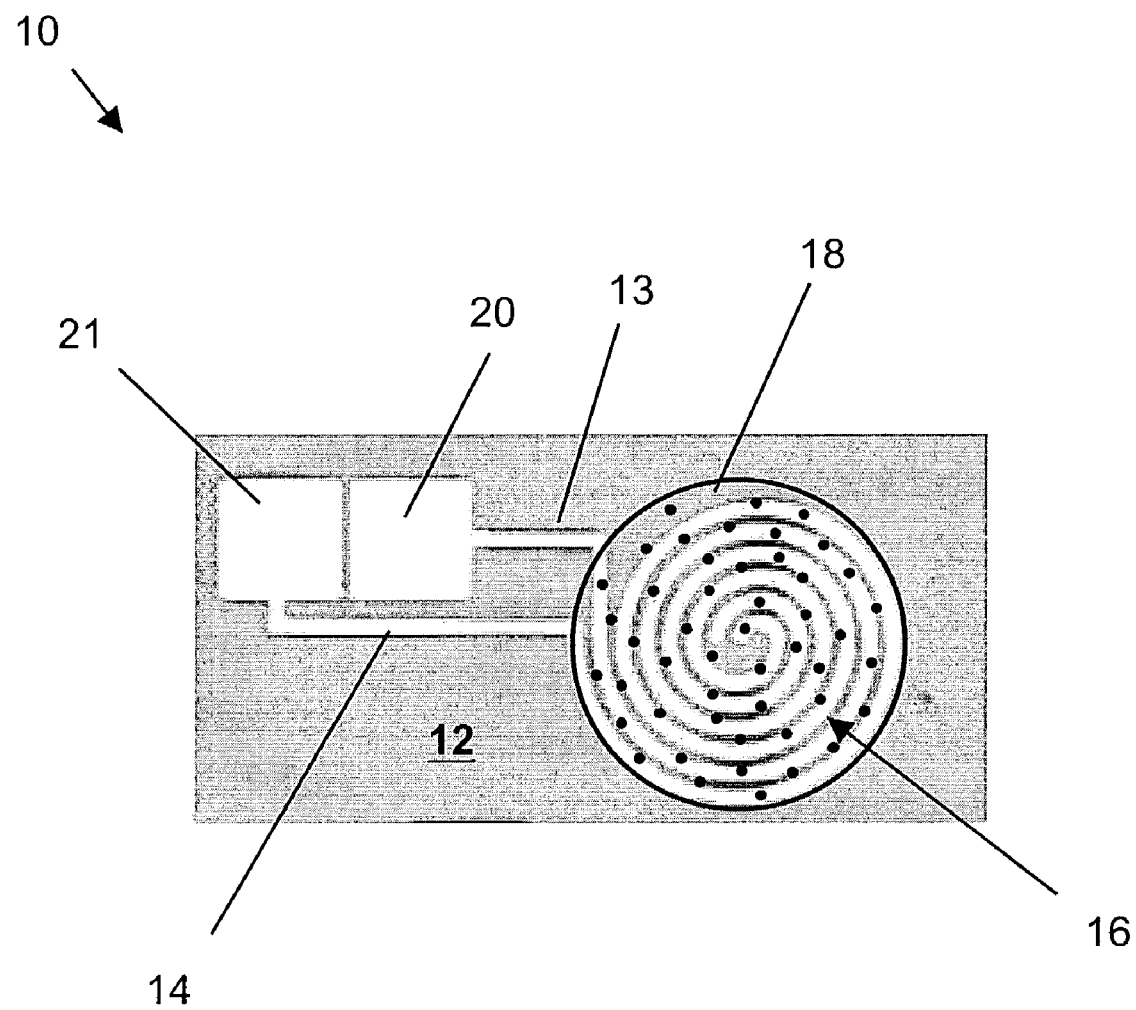
FIG. 4a illustrates a schematic plan view of a first example of a circular chemiresistor, according to the present invention.

FIG. 4a illustrates a schematic plan view of a first example of a circular chemiresistor, according to the present invention. Circular chemiresistor 10 comprises an electrically insulating substrate 12 with a pair of conductive lines 13, 14 disposed on the substrate, with each line having a distal end. The pair of distal ends conductive lines 13, 14 are arranged in a circle-filling geometry. A deposit of a chemically sensitive polymer 18 contacts the distal ends of the pair of conductive lines 13, 14. In this example, the circle-filling geometry comprises a dual-track (i.e., concentric) spiral 16. The proximal ends of lines 13, 14 are interconnected to bond pads 20, 21, respectively. Lines 13, 14 do not touch each other. By applying a voltage difference across bond pads 20 and 21, current can be made to flow in through one of the lines, passing through that part of the polymer coating 18 that is disposed on the surface of substrate 12 in-between lines 13 and 14, and then out through the other line. Measuring the steady state current flowing through this loop allows the average/bulk resistance of polymer coating 18 to be calculated by using Ohm's Law. Typically, direct current is used; however, oscillating current or transient currents may be used as well. The change in resistance is proportional to the concentration of vapor absorbed in the chemically sensitive polymer deposit 18.

Examples of suitable polymer matrices (i.e., hosts) for polymer film 18 are shown in Table 1.

TABLE 1

| Suitable Polymer Hosts | |
|---|---|
| poly(n-vinyl pyrrolidone) | PNVP |
| poly(vinyl alcohol) | PVA |
| poly(ethylene-vinyl acetate) | PEVA |
| poly(isobutylene) | PIB |
| poly(epichlorohydrin) | PECH |
| ethyl cellulose | EC |
| poly(chloroprene) | PCP |
| poly(diphenoxyphosphazine) | PDPP |
| poly(caprolactone) | PCL |

Those skilled in the art will understand that the polymer matrix can be selected to provide a high sensitivity or selectivity for detection of a particular VOC by matching the solubility parameter, $\delta$, of the polymer matrix with that of the VOC to be detected. For example, the polymer matrix PIB is useful for detecting VOCs having low values of $\delta$, which include non-polar VOCs such as isooctane, cyclohexane, m-xylene, toluene, TCE and acetone. On the other hand, the polymer matrix PVA is useful for detecting VOCs having larger values of $\delta$, which include polar VOCs such as ethanol, methanol, and water vapor.

The example of a circle-filling geometry illustrated in FIG. 4a is described as a "dual-track spiral". Here, we mean that there are two different spirals that have been nested inside of each other in a concentric fashion. The two concentric spiral patterns don't touch each other, but, rather, closely follow each other in a "parallel" fashion where the spacing/gap between the exterior edges of adjacent lines of each spiral remains uniform (in this example) along the path defined by the spiral. Hence, in this application, the phrases "dual-track spiral", "dual spiral", "concentric spiral" and "nested pair of spirals" all mean the same thing; an example of which is shown in FIG. 4a. Unless otherwise stated, when referring to the pair of conductive lines in contact with the polymer deposit 18, we mean, but don't always indicate, the "distal ends" of the pair of lines.

Electrically insulating substrate 12 may comprise silicon, silicon with a coating of silicon nitride or silicon dioxide, plastic, polymer, ceramic, pwb material, or other electrical insulating bulk material, or, alternatively, an insulating coating on a conductive substrate (e.g., silicon nitride, silicon oxide, silicon oxynitride, silicon carbide, silicate glass). Conducting lines 13, 14 may be thin-film or thick-film metallic traces, e.g., gold, silver, copper, aluminum, platinum, titanium, tungsten, or combinations thereof. The conductive material used for lines 13, 14 should be resistant to corrosion, attack, dissolution, or other damage from the solvent(s) used to dissolve/suspend the chemically sensitive polymer composite coating, or from the solidified coating itself. Platinum, which is particularly resistant to chemical attack by most chemicals including VOC's and water vapor, may be used for conducting lines 13, 14 and bond pads 20, 21. Coating 18 should be well adhered to conductive lines 13, 14.

The distal ends of conductive lines 13, 14 may be uniformly spaced apart from each other. The spacing (i.e., open gap) between adjacent lines 13, 14 may be less than or equal to approximately 100 microns, and may be less than or equal to approximately 50 microns. Alternatively, the spacing (i.e., open gap) between the exterior edges of adjacent lines 13, 14 may be less than or equal to approximately 30 microns; and may be greater than approximately 10 microns. Spacings less than 10 microns may have problems with shorting across conductive lines 13, 14 due to conduction through large clumps of agglomerated carbon (or metal) particles bridging across lines 13 and 14. The width of conductive lines 13, 14 may be less than or equal to approximately 50 microns. Alternatively, the line width may be less than or equal to approximately 30 microns. Alternatively, the line width may be may be greater than or equal to approximately 10 microns.

In FIG. 4A, the width of lines 13, 14 is 30 microns, and spacing between the centerlines of lines 13, 14 is 50 microns. The dual-track spiral pattern 16 comprises 3 full turns (rotations). Alternatively, the dual-track spiral 16 may comprise 1 turn, 2 turns, or more than 3 turns. The width of conductive lines 13, 14 may be variable, in the sense that they may get wider or narrower while moving along the spiral path. Likewise the gap/spacing between conductive lines 13, 14 may be variable, in the sense that they may get wider or narrower while moving along the spiral path.

The circle-filling geometry of the pair of electrodes 13, 14 shown in FIG. 4A (i.e., dual-track spiral 16) closely matches the circular shape of a drop of conductive ink, such as might be deposited by a micropipette or similar tool. In this sense, the electrode geometry is "circle-filling". In FIG. 4A, the contact area ratio is approximately equal to 50/(50+30)=0.63 (65%), which is more than twice the contact area ratio of the chemiresistors shown in FIGS. 1A, 1B and 2A, 2B. Concentric spiral-trace designs provide greater contact area between the electrode and polymer film, thereby providing lower and more stable baseline resistances than previously used linear-trace designs.

Figure 4B:
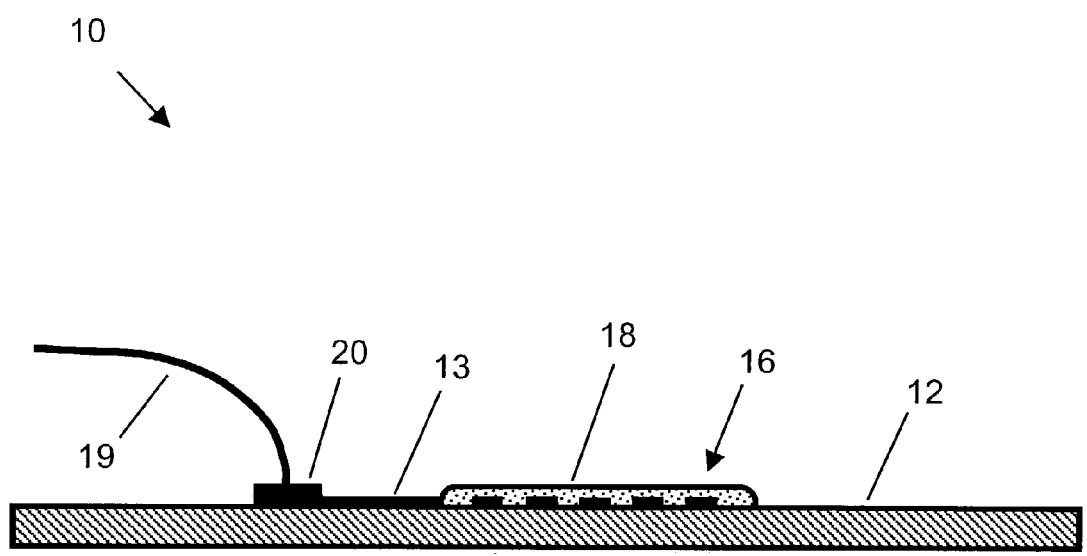
FIG. 4b illustrates a schematic cross-section view of the first example of a chemiresistor with a circular sensing element, according to the present invention.

FIG. 4b illustrates a schematic cross-section view of the first example of a circular chemiresistor, according to the present invention. A wirebond interconnection 19 has been made to bond pad 20.

Figure 5:
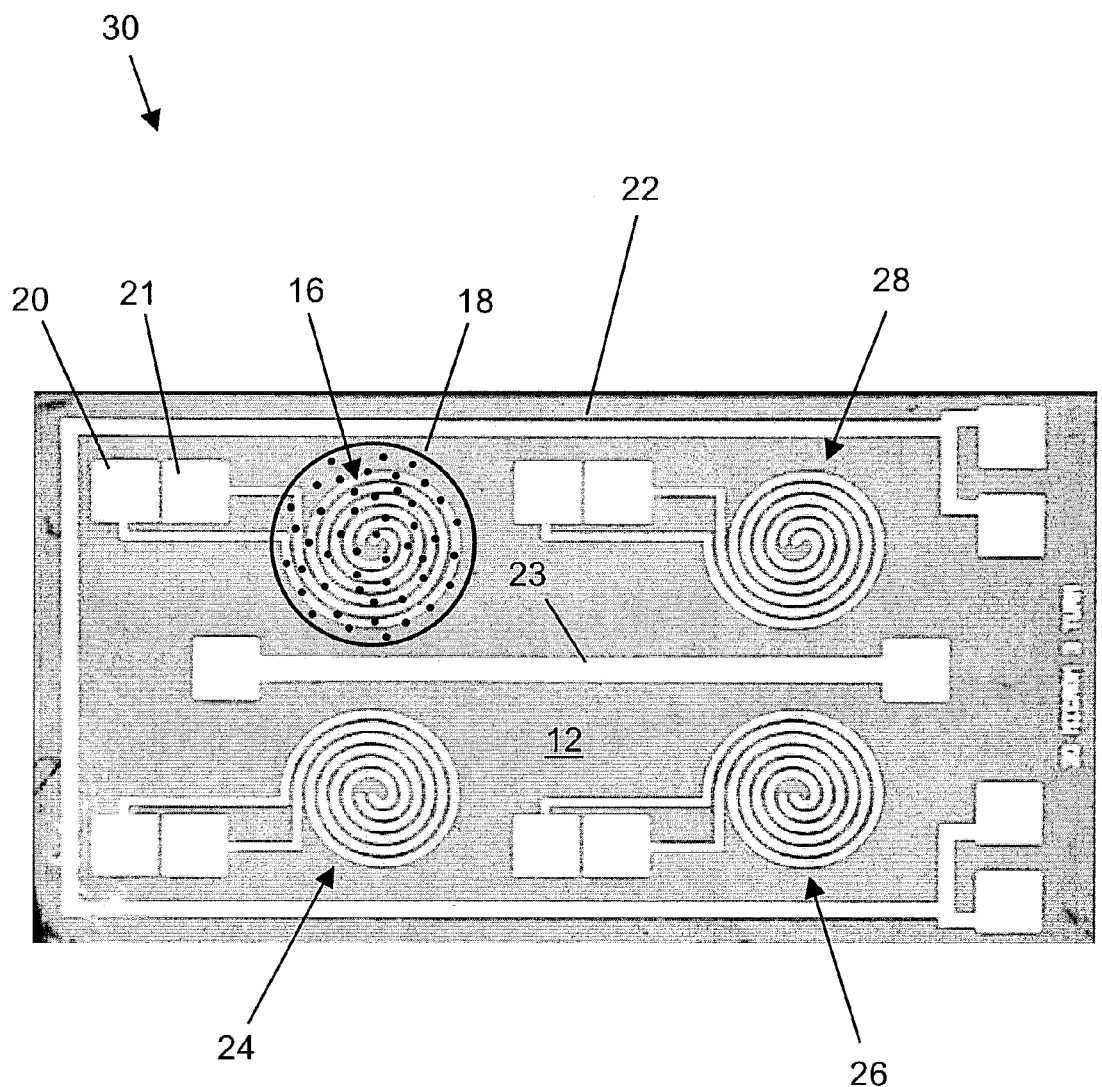
FIG. 5 illustrates a schematic plan view of a second example of a compact microchemical sensor comprising four circular chemiresistors, according to the present invention.

FIG. 5 illustrates a schematic plan view of a second example of a compact microchemical sensor comprising four circular chemiresistors, according to the present invention. Microchemical sensor 30 comprises an electrically insulating substrate 12, comprising four circular chemiresistors 16, 24, 26, 28, each chemiresistor comprising a dual-track, three-turn spiral geometry. Only one chemically sensitive polymer film 18 is illustrated. The outside diameter of each circular chemiresistor is approximately 1 mm. Resistance heating element 22 is disposed around the perimeter of substrate 12, and may be used to heat substrate 12 above room temperature to help reduce condensation of moisture onto the chemiresistors when the relative humidity is high. Resistance temperature sensor 23 is disposed in the center of substrate 12. Heating element 22 and temperature sensor 23 may be made of platinum. The four circular chemiresistors 16, 24, 26, 28 are disposed in-between the heating element 22 and temperature sensor 23 in a compact layout that provides uniform temperature control.

Figure 6:
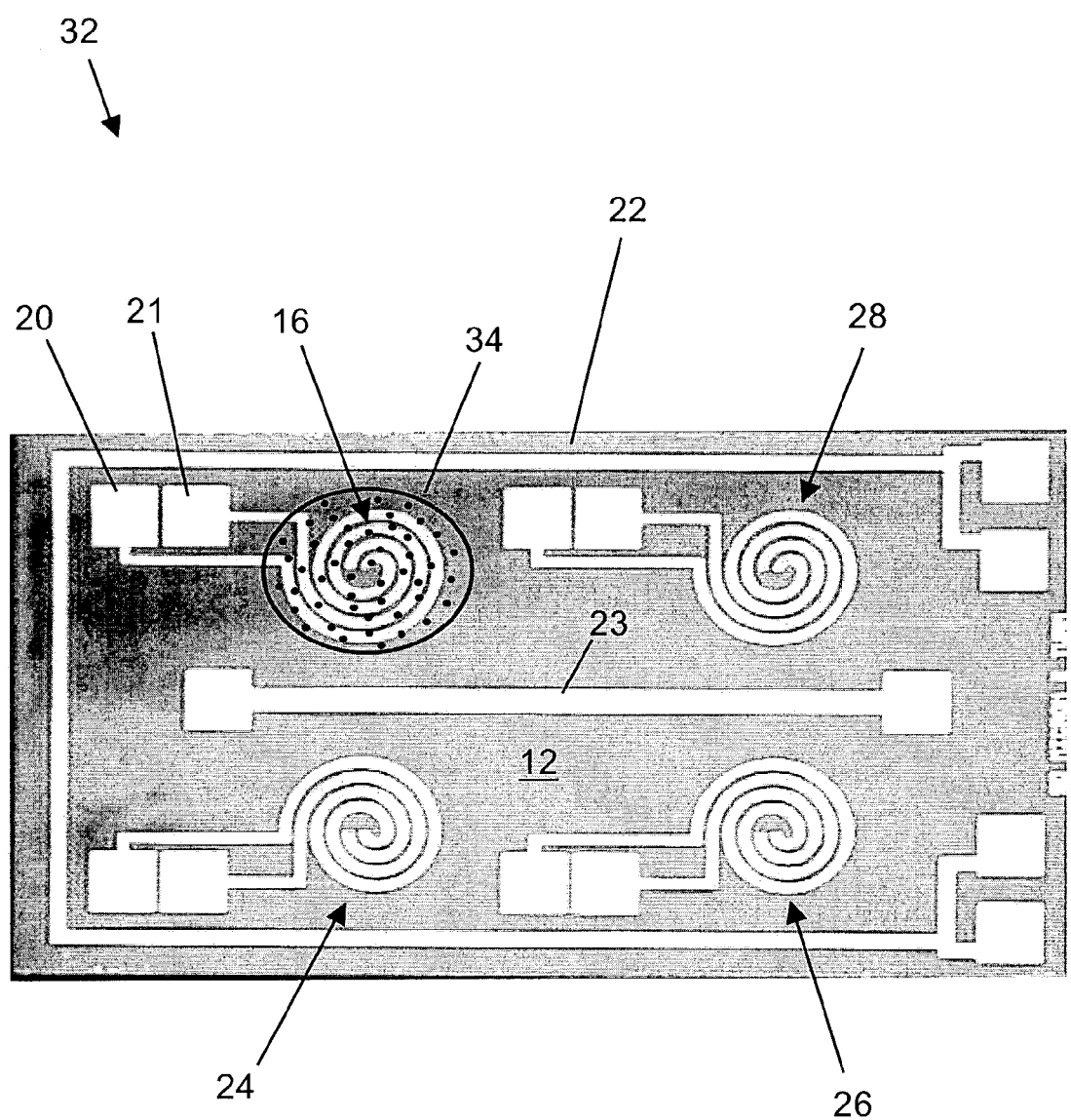
FIG. 6 illustrates a schematic plan view of a third example of a compact microchemical sensor comprising four circular chemiresistors, according to the present invention.

FIG. 6 illustrates a schematic plan view of a third example of a compact microchemical sensor comprising four circular chemiresistors, according to the present invention. Microchemical sensor 32 comprises an electrically insulating substrate 12, comprising four circular chemiresistors 16, 24, 26, 28, each chemiresistor comprising a dual-track, two-turn spiral geometry. The outside diameter of each circular chemiresistor is approximately 0.8 mm. Only one chemically sensitive polymer film 34 is illustrated, which has an elliptical shape.

Figure 7A:
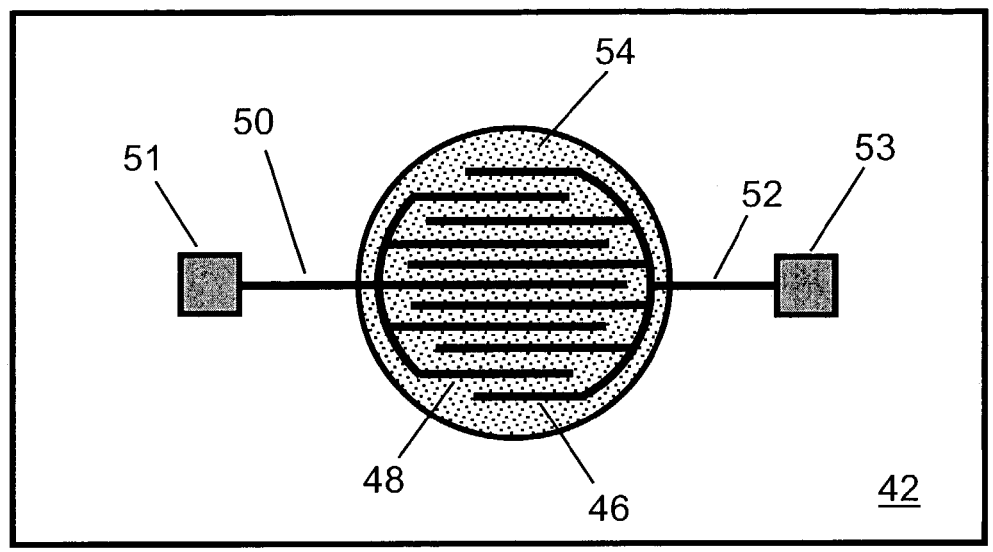
FIG. 7A illustrates a schematic plan view of a fourth example of a circular chemiresistor, according to the present invention.

FIG. 7A illustrates a schematic plan view of a fourth example of a circular chemiresistor, according to the present invention. Chemiresistor 40 comprises an electrically insulating substrate 42 with a circularly-shaped chemically sensitive polymer film 54 contacting a plurality of interdigitated electrodes 46 and 48, arranged in a circle-filling geometry. A pair of conductive lines 50, 52 disposed on the substrate electrically connect bond pads 51 and 53 to interdigitated electrodes 46 and 48, respectively.

Figure 7B:
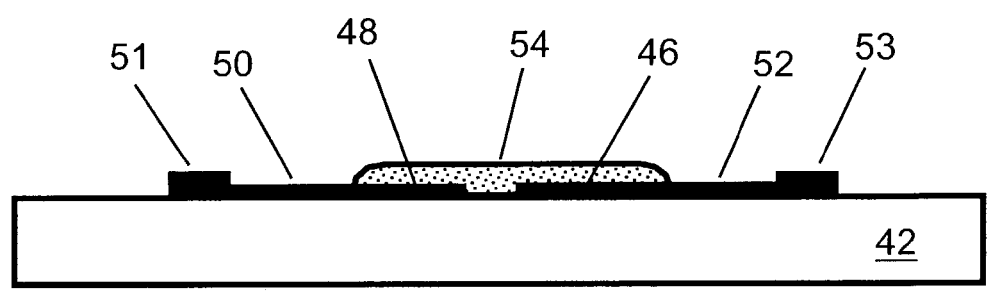
FIG. 7B illustrates a schematic cross-section view of the fourth example of a circular chemiresistor, according to the present invention.

FIG. 7B illustrates a schematic cross-section view of the fourth example of a circular chemiresistor, according to the present invention.

Figure 7C:
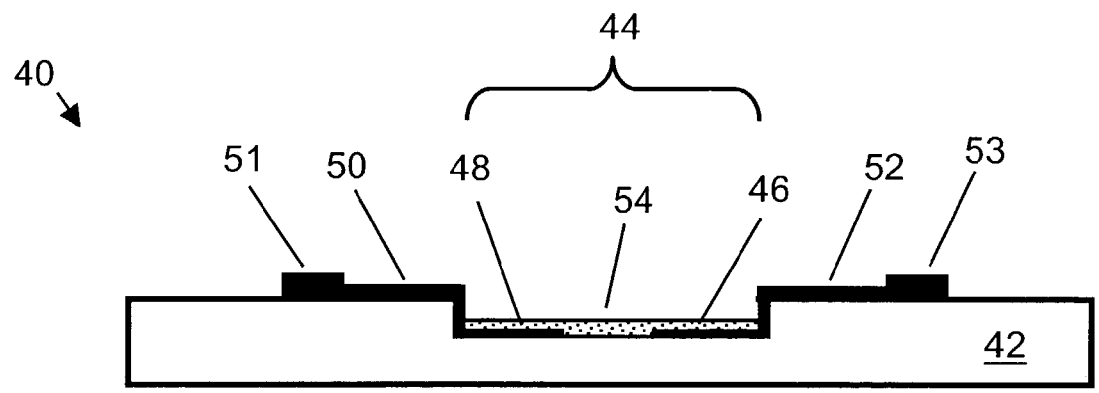
FIG. 7C illustrates a schematic cross-section view of the fourth example of a circular chemiresistor, wherein the substrate has a recessed, open cavity, according to the present invention.

FIG. 7C illustrates a schematic cross-section view of the fourth example of a circular chemiresistor wherein the substrate has a recessed, open cavity, according to the present invention. Chemically sensitive polymer 54 is disposed inside of cavity 44 (i.e., basin, recess, through), which confines the outer perimeter of polymer deposit 54 to have a circular shape that closely matches the circle-filling geometry of interdigitated electrodes 46 and 48. The depth of cavity 44 may be approximately 100 microns, and the thickness of film 54 may be approximately 10 microns. Alternatively, the depth of cavity 44 may be approximately 10–100 microns. Alternatively, the thickness of film 54 may be approximately 1–10 microns. Alternatively, the thickness of film 54 may be approximately 10–100 microns, or it may be thicker than 100 microns. The volume of cavity may be less than or equal to approximately 10 microliters. Alternatively, the volume of cavity may be less than or equal to approximately 1 microliters.

In one or more embodiments of the present invention, the recessed, open cavity may comprise one or more geometries selected from the group consisting of a channel, a trench, a trough, a narrow channel, a straight channel, a curved channel, a channel with a flat bottom, a channel with a curved bottom, a channel with tapered sidewalls, and a channel formed into the shape of a spiral.

Figure 7D:
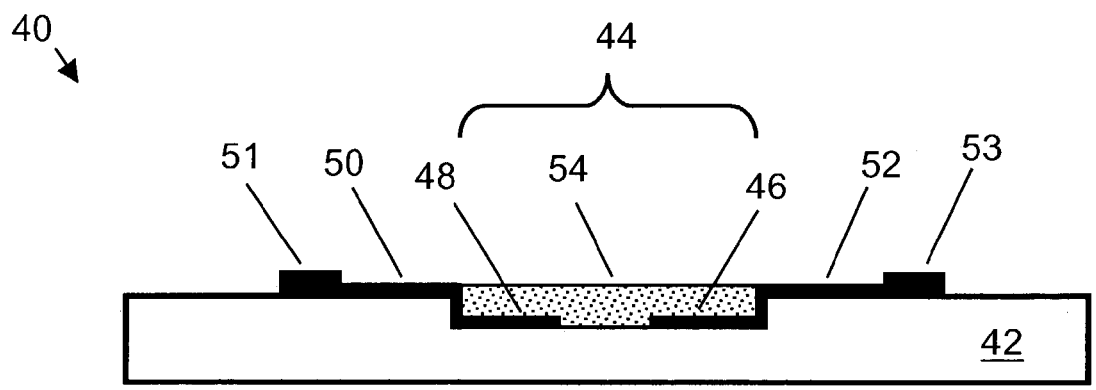
FIG. 7D illustrates a schematic cross-section view of the fourth example of a circular chemiresistor, wherein the substrate has a recessed, open cavity, according to the present invention.

FIG. 7D illustrates a schematic cross-section view of the fourth example of a circular chemiresistor wherein the substrate has a recessed, open cavity, according to the present invention. Chemically sensitive polymer film 54 may substantially fill cavity 44, or may completely fill cavity 44 (as illustrated in FIG. 7D), or may somewhat overfill cavity 44.

Figure 8A:
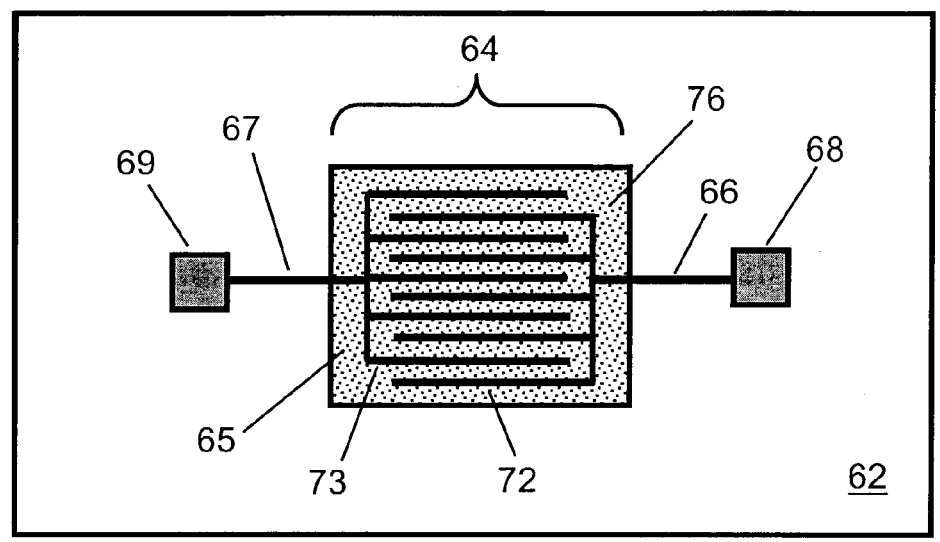
FIG. 8A illustrates a schematic plan view of a fifth example of a chemiresistor, wherein the substrate has a recessed, open cavity, according to the present invention.

FIG. 8A illustrates a schematic plan view of a fifth example of a chemiresistor, wherein the substrate has a recessed, open cavity, according to the present invention. A plurality of interdigitated electrodes 72 and 73 are disposed on the floor 65 of square cavity 64. The plurality of interdigitated electrodes 72 and 73 may substantially cover the floor 65 of cavity 64. A pair of conductive lines 66, 67 disposed on substrate 62 electrically connect bond pads 68, 69 to interdigitated electrodes 72, 73, respectively. The shape of cavity 64 may be a square, rectangular, triangular, hexagonal, or polygonal shape. Chemically sensitive polymer film 76 contacts the plurality of interdigitated electrodes 72 and 73.

In one or more embodiments of the present invention, the pair of distal ends of the conductive lines that are disposed inside of the recessed open cavity may be arranged in a cavity-filling geometry (i.e., circle-filling geometry, square-filling geometry, rectangle-filling geometry, etc.), meaning that more than 50% of the area of the floor of the cavity is filled with the distal ends of the pair of conductive lines.

Figure 8B:
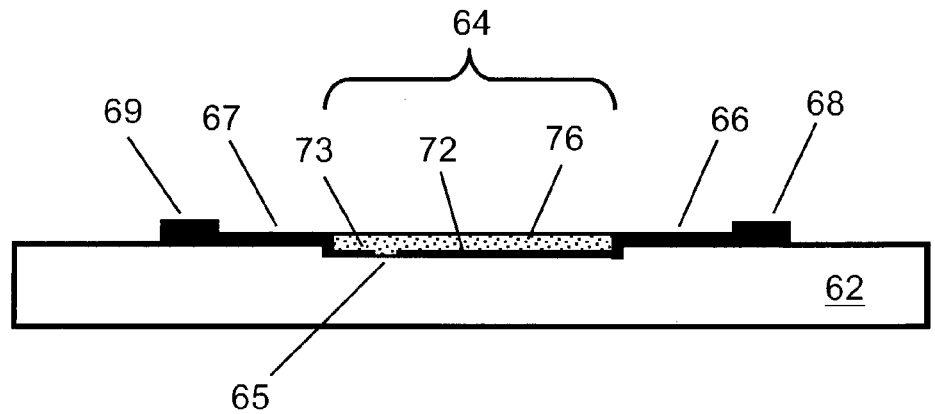
FIG. 8B illustrates a schematic cross-section view of a fifth example of a chemiresistor, wherein the substrate has a recessed, open cavity, according to the present invention.

FIG. 8B illustrates a schematic cross-section view of a fifth example of a chemiresistor, wherein the substrate has a recessed, open cavity, according to the present invention. The depth of cavity 64 may be from 1–10 microns, and chemically sensitive polymer film 76 may substantially fill cavity 64.

Figure 9A:
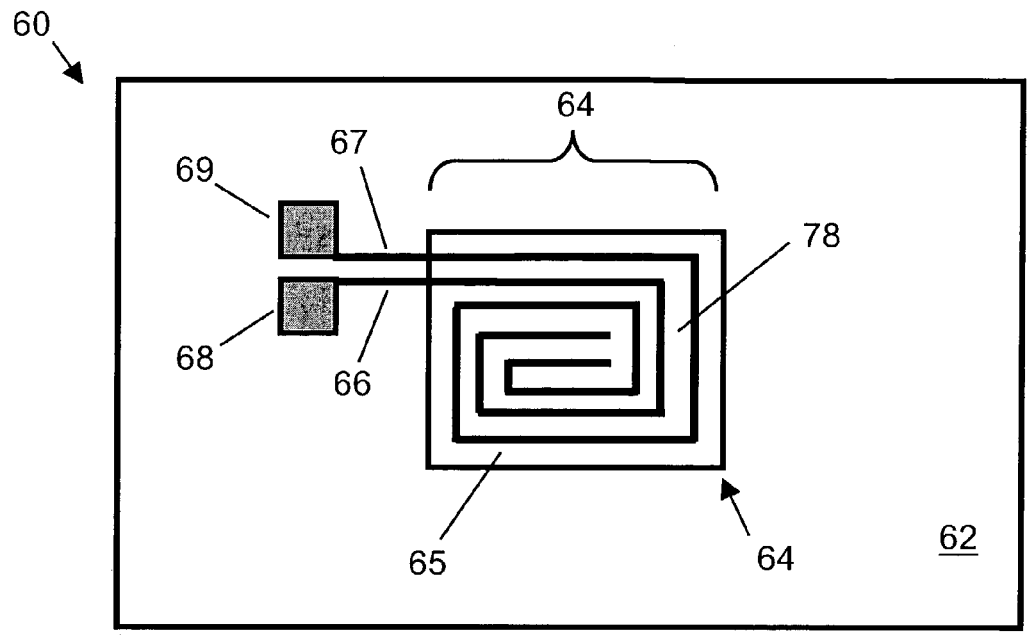
FIG. 9A illustrates a schematic plan view of a sixth example of a chemiresistor, wherein the substrate has a recessed, open cavity, according to the present invention.

FIG. 9A illustrates a schematic plan view of a sixth example of a chemiresistor, wherein the substrate has a recessed, open cavity, according to the present invention. Cavity 65 has a rectangular shape (which includes a square shape). A plurality of electrodes 66 and 67 are disposed on the floor 65 of cavity 64, and are arranged in a concentric, dual-track block spiral geometry 78, which substantially fills the floor of cavity 64 and contacts electrodes 66 and 67. Here, "block spiral" refers to the shape drawn in FIG. 9A where each line segment that makes up the block spiral is straight, until it meets a corner, where it turns 90 degrees and travels another straight segment.

Figure 9B:
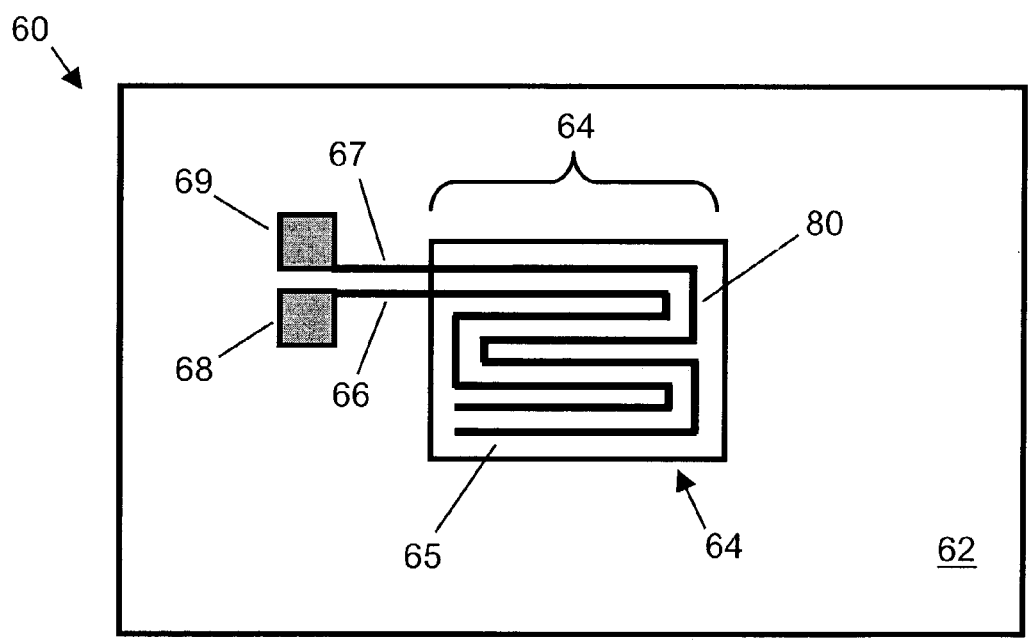
FIG. 9B illustrates a schematic plan view of a seventh example of a chemiresistor, wherein the substrate has a recessed, open cavity, according to the present invention.

FIG. 9B illustrates a schematic plan view of a seventh example of a chemiresistor, wherein the substrate has a recessed, open cavity, according to the present invention. A plurality of electrodes 66 and 67 are disposed on the floor 65 of cavity 64, and are arranged in a dual-track meandering or serpentine (i.e., boustrophedon) geometry 80, which substantially fills the floor of cavity 64 and contacts electrodes 66 and 67. Patterns 78 and 80 are examples of a square-filling geometry.

With reference to the electrode geometries illustrated in FIGS. 9A and 9B, other space-filling curves may be used to substantially cover the floor 65 of cavity 64. Other space-filling curves that may be used include the class of curves called "Hilbert" curves and "Peano" curves, and their variations and relatives. These self-similar curves can be made to cover the area as fine as possible (without limit) depending on the number of sub-regions that the original area is divided into. Although these families of curves are conventionally referred to as "space-filling" curves, in this context we would describe them as "area-filling" or "cavity-filling" curves.

Figure 9C:
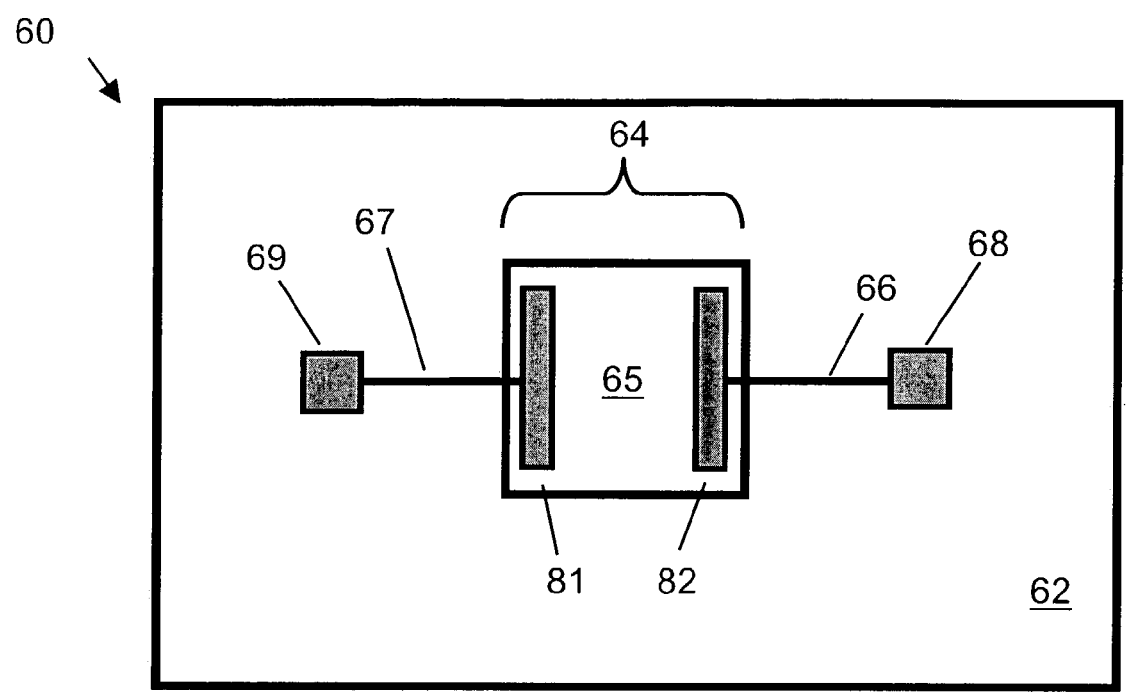
FIG. 9C illustrates a schematic plan view of an eighth example of a chemiresistor, wherein the substrate has a recessed, open cavity, according to the present invention.

FIG. 9C illustrates a schematic plan view of an eighth example of a chemiresistor, wherein the substrate has a recessed, open cavity, according to the present invention. A plurality of electrodes 66 and 67 are connected to a pair of long and narrow electrodes 81 and 82 that are disposed at opposite sides of cavity 64 on cavity floor 65.

Figure 10A:
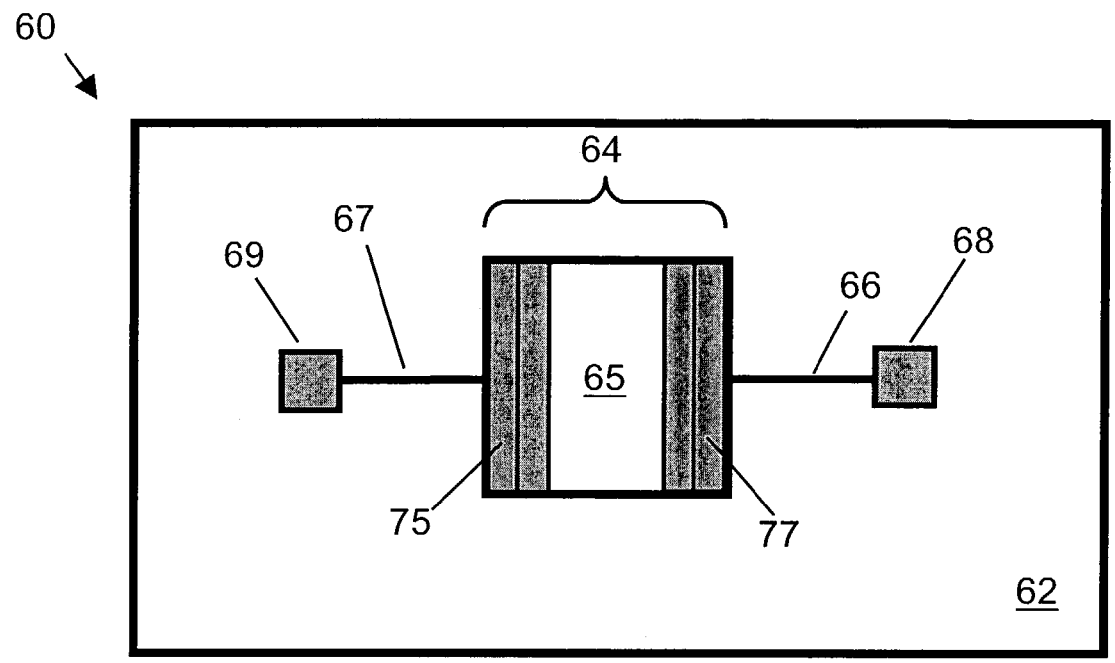
FIG. 10A illustrates a schematic plan view of a ninth example of a chemiresistor, wherein the substrate has a recessed, open cavity, according to the present invention.

FIG. 10A illustrates a schematic plan view of a ninth example of a chemiresistor, wherein the substrate has a recessed, open cavity, according to the present invention. A plurality of conductors 66 and 67 are connected to a pair of long and narrow electrodes 75 and 77 that are disposed at opposite sides of cavity 64.

Figure 10B:
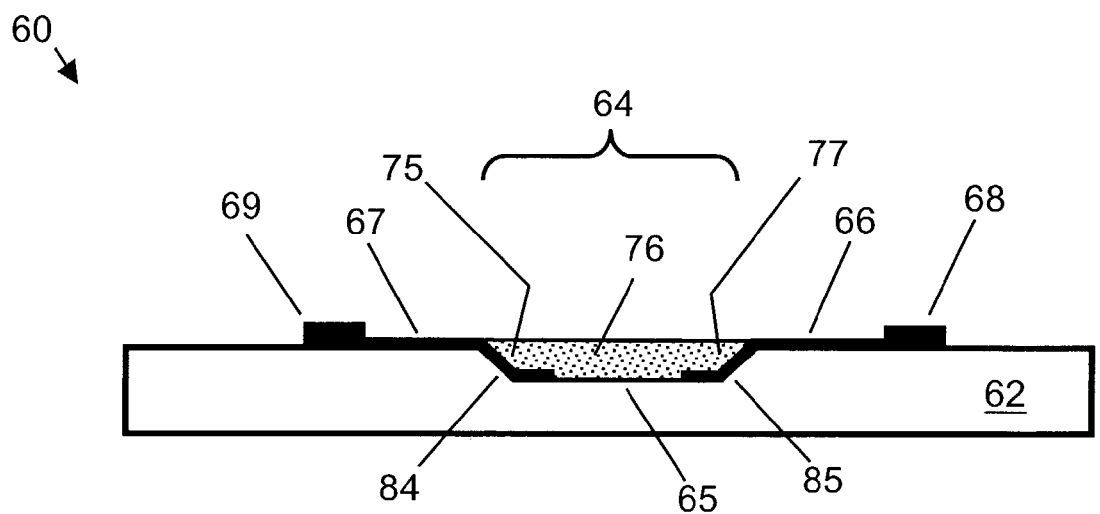
FIG. 10B illustrates a schematic cross-section view of the ninth example of a chemiresistor, wherein the substrate has a recessed, open cavity, according to the present invention.

FIG. 10B illustrates a schematic cross-section view of the ninth example of a chemiresistor, wherein the substrate has a recessed, open cavity, according to the present invention. Sidewalls 84 and 85 of cavity 64 may be sloped at an angle with respect to floor 65. Electrodes 75 and 77 are disposed on the sloped sidewalls 84 and 85.

Figure 11A:
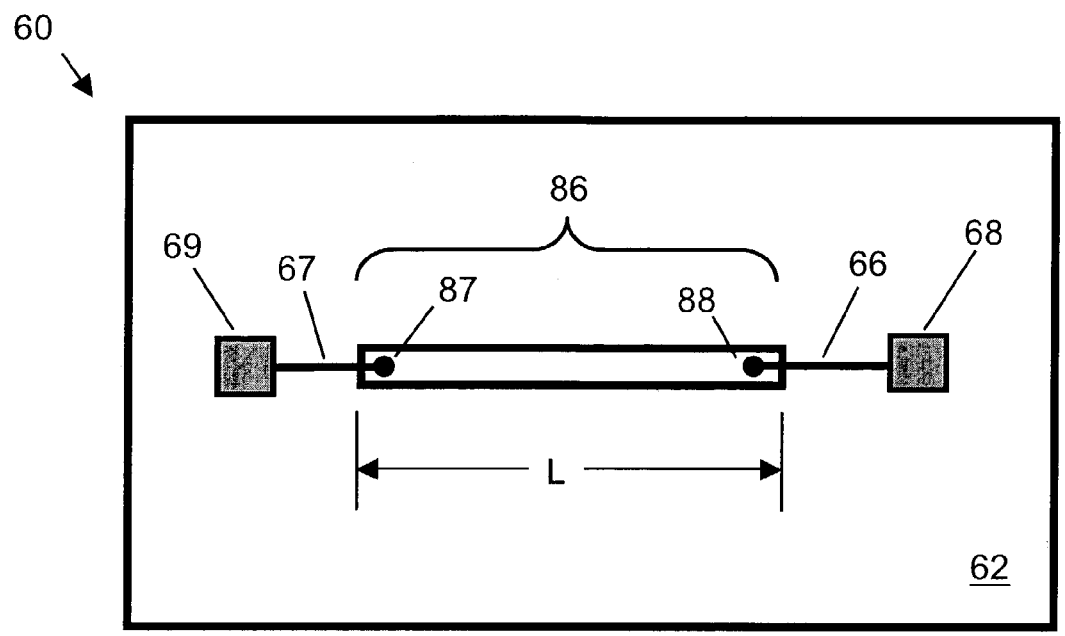
FIG. 11A illustrates a schematic plan view of a tenth example of a chemiresistor, wherein the substrate has a recessed, open cavity, according to the present invention.

FIG. 11A illustrates a schematic plan view of a tenth example of a chemiresistor, wherein the substrate has a recessed, open cavity, according to the present invention. A pair of conductors 66 and 67 connects to a pair of electrodes 87 and 87 that are disposed at opposite ends of a long and narrow cavity 86 (i.e., trench, trough, channel), where the distance between the pair of electrodes is L.

Figure 11B:
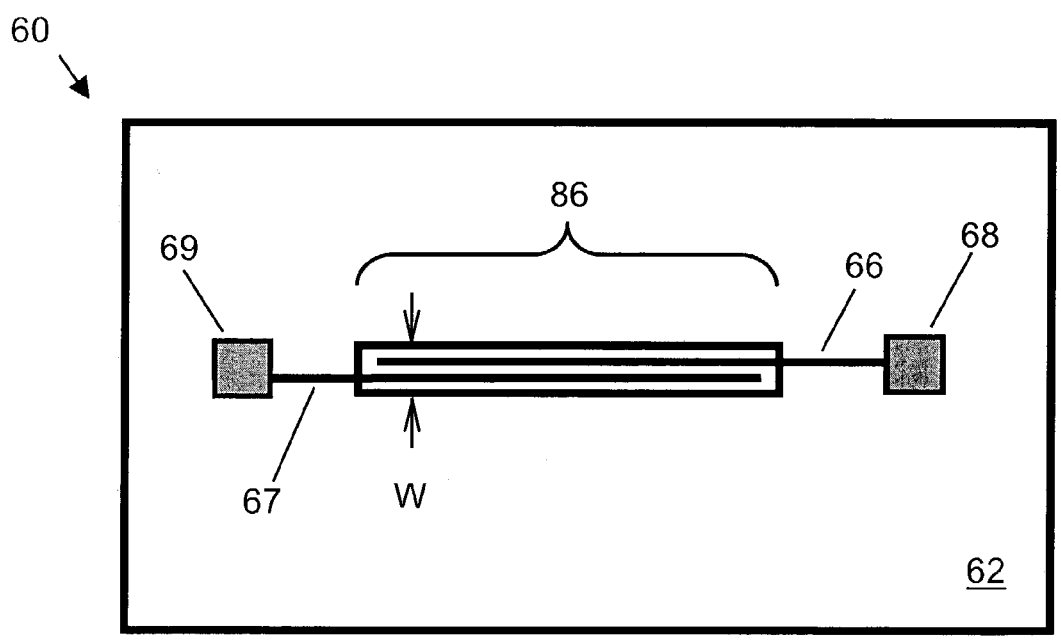
FIG. 11B illustrates a schematic plan view of an eleventh example of a chemiresistor, wherein the substrate has a recessed, open cavity, according to the present invention.

FIG. 11B illustrates a schematic plan view of an eleventh example of a chemiresistor, wherein the substrate has a recessed, open cavity, according to the present invention. A pair of electrodes 66 and 67 form a linear interdigitated geometry (i.e., side-by-side) that runs almost the entire length of cavity 86, where the distance between the pair of electrodes is approximately equal to W/2. Here, the distance between the pair of electrodes is much shorter than compared to the example shown in FIG. 11A. The width, W, of cavity 86 may be less than approximately 250 microns. Alternatively, the width, W, of cavity 86 may be less than approximately 150 microns. Alternatively, the width, W, of cavity 86 may be less than approximately 100 microns. Alternatively, the width, W, of cavity 86 may be chosen such that a drop of chemiresistive ink deposited at one or more locations in the cavity 86 will wick by capillary forces into other regions of cavity 86. Alternatively, the entire volume of cavity 86 may be filled with chemiresistive ink via capillary wicking.

Figure 12:
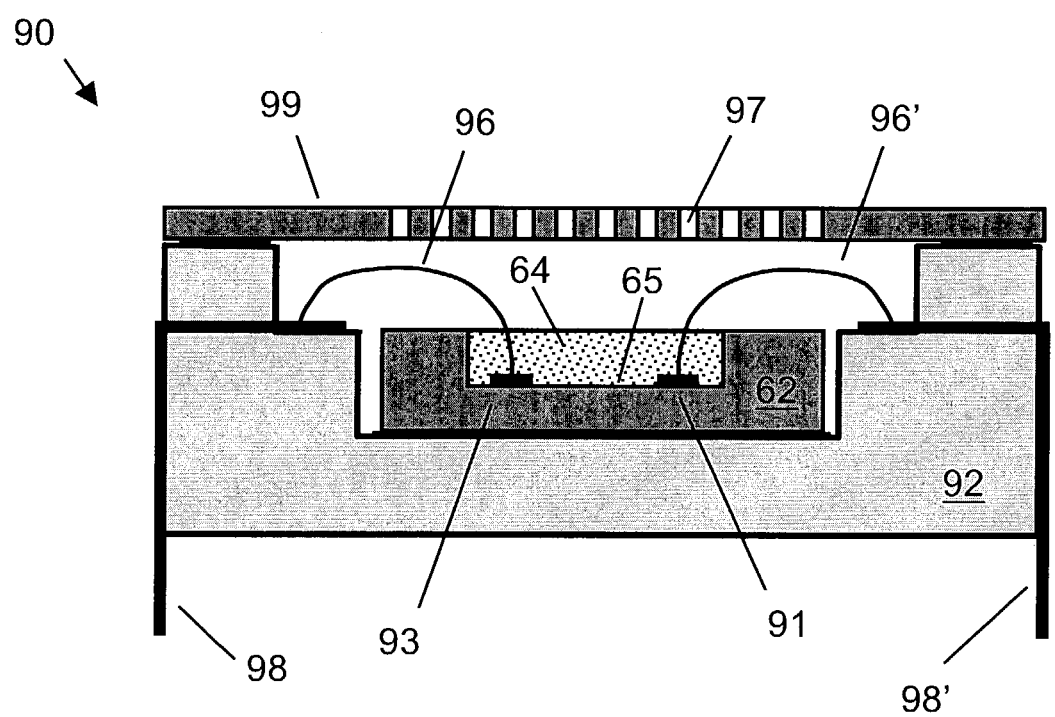
FIG. 12 illustrates a schematic cross-section view of the twelfth example of a chemiresistor, wherein the substrate has a recessed, open cavity, according to the present invention.

FIG. 12 illustrates a schematic cross-section view of the twelfth example of a chemiresistor, wherein the substrate has a recessed, open cavity, according to the present invention. Cavity 64 is recessed into substrate 62, which has a pair of electrodes 91 and 93 disposed on the floor 65 of cavity 64. Substrate 64 is die attached to a plastic or ceramic package 92, which has a pair of external leads 98 and 98'. Wirebond interconnections 96 and 96' interconnect electrodes 91 and 93 to external leads 98 and 98', respectively. A cover lid 99 with perforations 97 may be attached to package 92 to provide mechanical protection for the wirebonds 96, 96' and polymer film 64, while allowing vapors to access polymer film 64. The wirebond interconnections 96, 96' would likely be made before polymer film 64 is deposited, although this order could be reversed by using a laser, for example, to ablate an opening in polymer film 64 to expose the underlying electrodes 91 and 93 after polymer film 64 has been deposited.

Figure 13A:
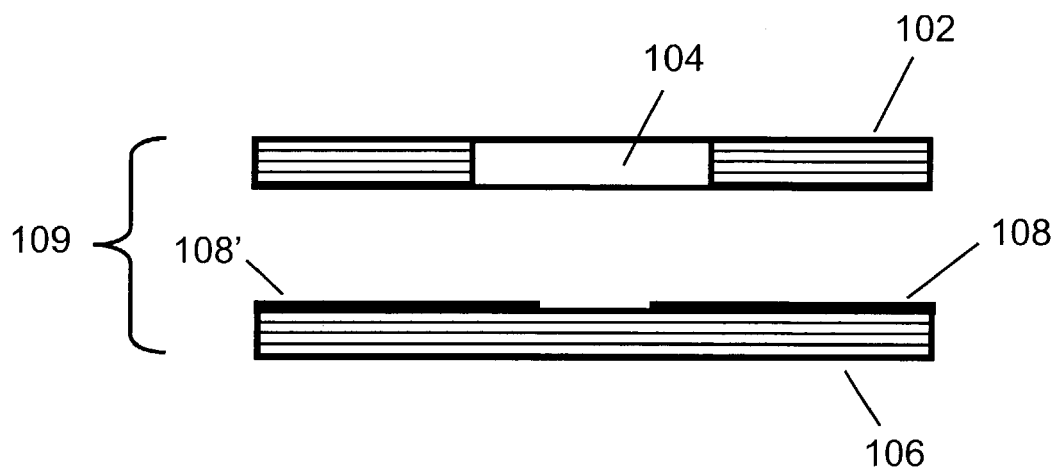
FIG. 13A illustrates a schematic cross-section view of a method for fabricating a chemiresistor with a recessed, open cavity, according to the present invention.

FIG. 13A illustrates a schematic cross-section view of a method for fabricating a chemiresistor with a recessed, open cavity, according to the present invention. Chemiresistor 110 comprises two separate plates 102 and 106 that will be bonded together. Upper plate 102 has a through hole or aperture 104. Lower plate 106 has a pair of conducting lines or traces 108, 108' disposed on the upper surface of lower plate 106. Plates 102 and 106 can comprise a multilayered material, such as a printed wiring board (pwb) material, or a Low-Temperature Cofired Ceramic (LTCC) or High-Temperature Cofired Ceramic (HTCC) material. Referring now to LTCC or HTCC plates 102 and 106, respectively, may each comprise a single layer of LTCC/HTCC material (e.g., green tape), or, alternatively, may each comprise multiple layers of green tape that is subsequently laminated and bonded together to form a single monolithic layer. A common thickness for a single sheet of green tape is approximately 100 microns. Accordingly, plates 102 and 106 may each be made from a single sheet of approximately 100 micron thick green tape. Aperture 104 can be formed by punching or cutting out a thru-hole in plate 102. Conducting lines 108, 108' can be formed by thin-film or thick-film techniques (e.g., screen printing using conductive inks or pastes). Additionally, other features may be fabricated on the upper surface of lower plate 106, such as a thin film resistive heating strip and/or a thin film temperature sensor (not shown), which become hidden (i.e., embedded) after the two plates are joined together.

The cost of fabricating ceramic packages can be reduced by using cofired ceramic multilayer packages. Multilayer packages are presently used in many product categories, including leadless chip carriers, pin-grid arrays (PGA's), side-brazed dual-in-line packages (DIP's), flatpacks, and leaded chip carriers. Depending on the application, 5–40 layers of dielectric layers can be used, each having printed signal traces, ground planes, and power planes. Each signal layer can be connected to adjacent layers above and below by conductive vias passing through the dielectric layers.

Electrically conducting metallized traces, thick-film resistors, and solder-filled vias or Z-interconnects are conventionally made by thick-film metallization techniques, including screen-printing. Multiple layers are printed, vias-created, stacked, collated, and registered. The layers are then joined together (e.g. laminated) by a process of burnout, followed by firing at elevated temperatures. Burnout at 350–600 C first removes the organic binders and plasticizers from the substrate layers and conductor/resistor pastes. After burnout, these parts are fired at much higher temperatures, which sinters and densifies the glass-ceramic substrate to form a dense and rigid insulating structure. Glass-forming constituents in the layers can flow and fill-in voids, corners, etc.

Two different cofired ceramic systems are conventionally used, depending on the choice of materials: high-temperature cofired ceramic (HTCC), and low-temperature cofired ceramic (LTCC). HTCC systems typically use alumina substrates; are printed with molybdenum-manganese or tungsten conducting traces; and are fired at high temperatures, from 1300 to 1800 C. LTCC systems use a wide variety of glass-ceramic substrates; are printed with Au, Ag, or Cu metallizations; and are fired at lower temperatures, from 600 C to 1300 C. After firing, the semiconductor die is attached to the fired HTCC (or LTCC) body; followed by wirebonding. Finally, the package is lidded and sealed by attaching a metallic, ceramic, or glass cover lid with a braze, a frit glass, or a solder seal, depending on the hierarchy of thermal processing and on performance specifications.

Figure 13B:
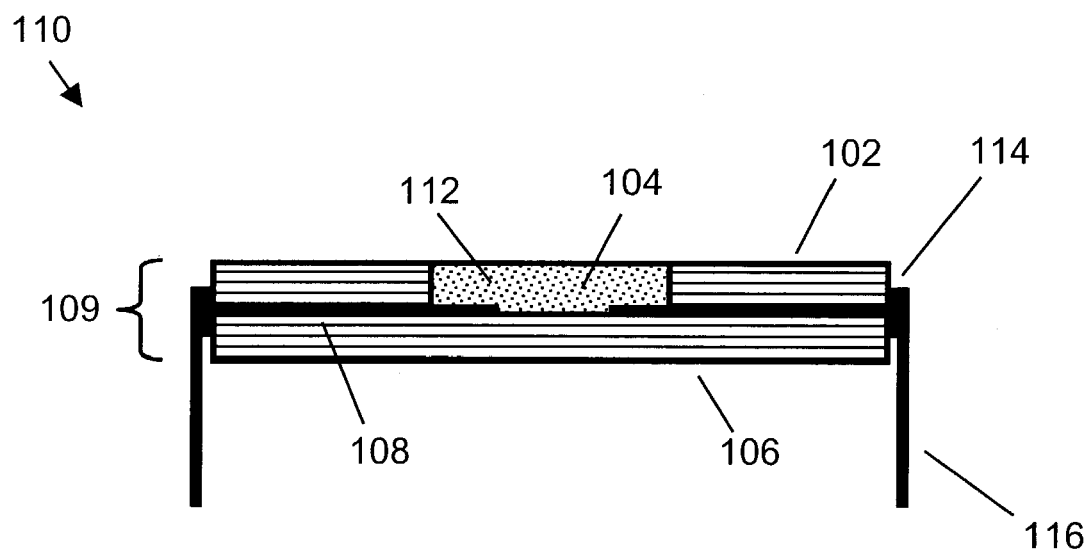
FIG. 13B illustrates a schematic cross-section view of a thirteenth example of a chemiresistor, wherein the substrate has a recessed, open cavity, according to the present invention.

FIG. 13B illustrates a schematic cross-section view of a thirteenth example of a chemiresistor, wherein the substrate has a recessed, open cavity, according to the present invention. Here, upper plate 102 and lower plate 106 (see FIG. 13A) have been joined together using heat and pressure (depending on the type of multi-layered material used, e.g., pwb, LTCC, HTCC). After plates 102 and 106 have been laminated and bonded to form a monolithic structure 109, bond pads 114 and external leads 116 can be attached (e.g., by brazing). Then, chemically sensitive polymer 112 can be deposited inside of cavity 104, contacting the distal ends of electrodes 108, 108'. With this type of multi-layered, laminated construction, conducting lines 108,108' are substantially embedded inside of the consolidated material. Polymer layer 112 can substantially fill cavity 104 (as illustrated), or may only partially fill cavity 104 (not shown). Alternatively, lower plate 106 can be made of silicon, and the upper plate 102 made of glass. In this case, anodic bonding can be used to join the silicon and glass plates together to make a monolithic structure.

Figure 13C:
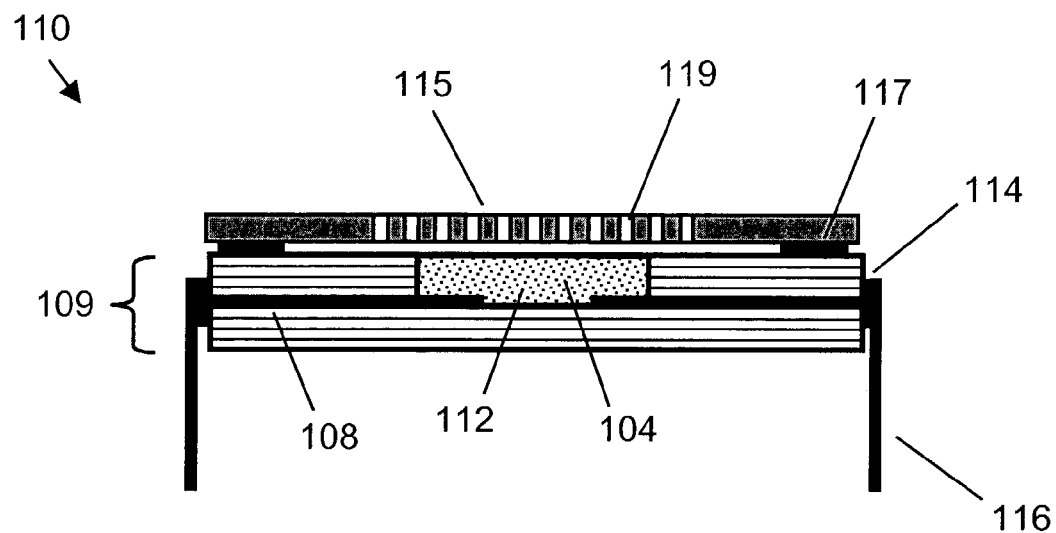
FIG. 13C illustrates a schematic cross-section view of the ninth example of a chemiresistor, wherein the substrate has a recessed, open cavity, according to the present invention.

FIG. 13C illustrates a schematic cross-section view of the ninth example of a chemiresistor, wherein the substrate has a recessed, open cavity, according to the present invention. Here, a cover lid 115 has been attached with an adhesive sealant 117 to the upper surface of the monolithic structure 109 after polymer film 112 has been deposited inside of cavity 104. Cover lid 115 may have perforations 119 to allow vapors to access the chemiresistor sensing element disposed underneath the lid.

Figure 14A:
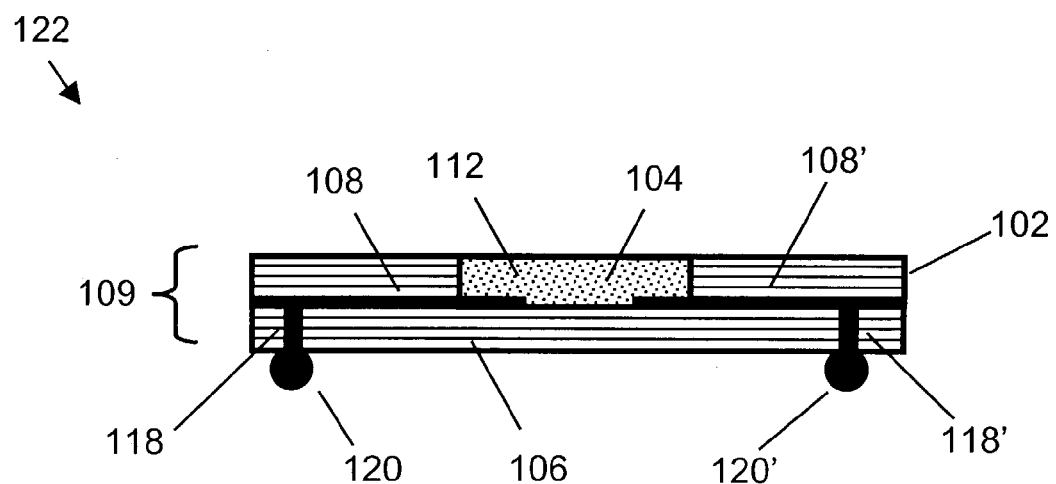
FIG. 14A illustrates a schematic cross-section view of a fourteenth example of a chemiresistor, wherein the substrate has a recessed, open cavity, according to the present invention.

FIG. 14A illustrates a schematic cross-section view of a fourteenth example of a chemiresistor, wherein the substrate has a recessed, open cavity, according to the present invention. Lower plate 106 has a pair of conductive vias 118, 118' that connect conductive lines 108, 108' to conductive balls 120, 120', which are attached to the lower surface of monolithic structure 109. Conductive balls 120, 120' may be made of solder or a conductive polymer, and may be arranged in a Ball Grid Array (BGA) format.

Figure 14B:
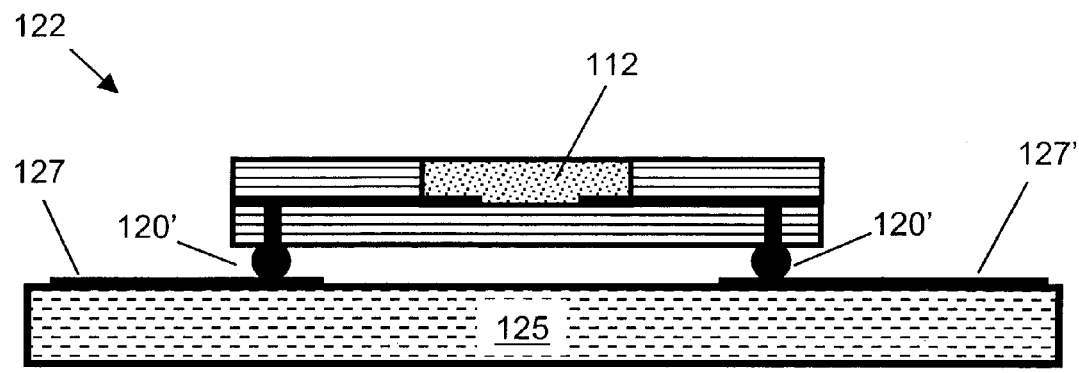
FIG. 14B illustrates a schematic cross-section view of a fifteenth example of a chemiresistor with a recessed, open cavity, that is mounted on a printed wiring board, according to the present invention.

FIG. 14B illustrates a schematic cross-section view of a fifteenth example of a chemiresistor with a recessed, open cavity, that is mounted on a printed wiring board, according to the present invention. Conductive balls 120, 120' of chemiresistor 122 are interconnected to conductive lines 127, 127' disposed on printed wiring board 125. In this sense, chemiresistor 122 is "flip-chip" mounted to board 125 (even though the active side (i.e., polymer film 112) of the "chip" (i.e., chemiresistor 122) is facing away from the board).

Figure 14C:
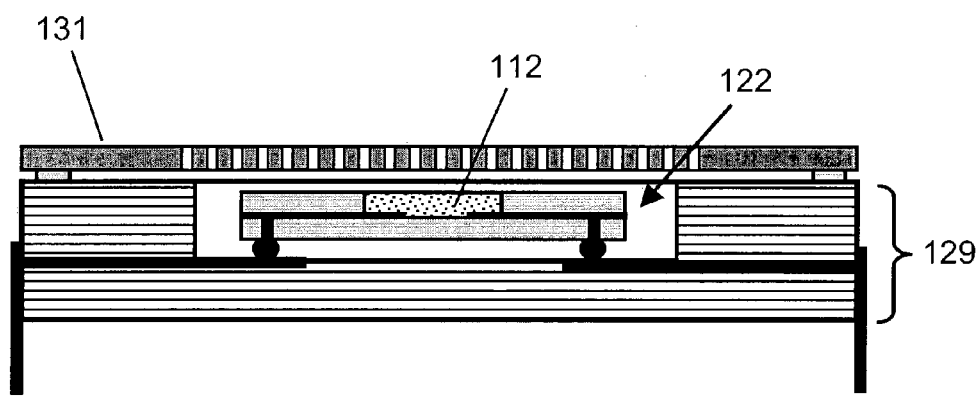
FIG. 14C illustrates a schematic cross-section view of a fifteenth example of a chemiresistor with a recessed, open cavity; mounted inside of a ceramic package, according to the present invention.

FIG. 14C illustrates a schematic cross-section view of a fifteenth example of a chemiresistor with a recessed, open cavity; mounted inside of a ceramic package, according to the present invention. Chemiresistor 122 is flip-chip mounted to LTCC package 129, and then cover lid 131 with perforations is attached. A piece of adhesive tape (not shown) can be placed across the perforation of cover lid 131 to protect chemically sensitive polymer 112 until use, at which time the tape is removed to expose the active area (i.e., polymer film 112).

Figure 14D:
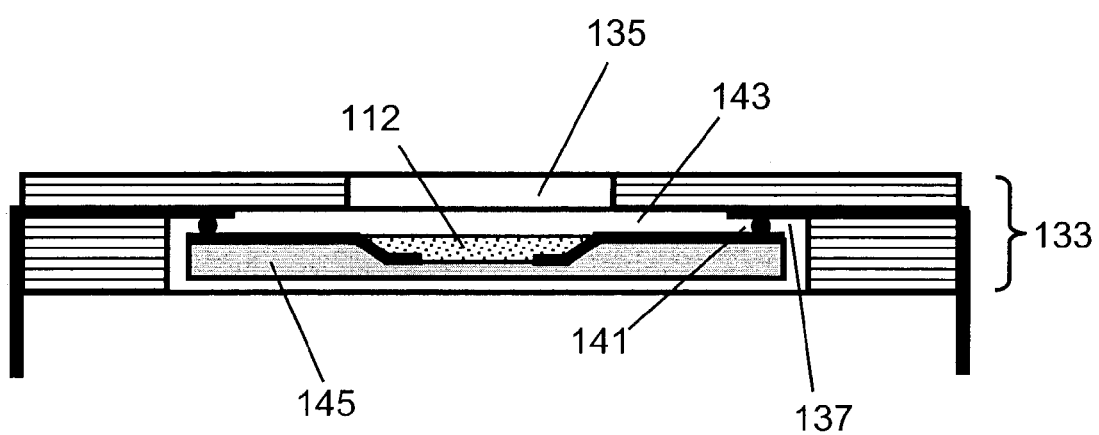
FIG. 14D illustrates a schematic cross-section view of a sixteenth example of a chemiresistor with a recessed, open cavity; mounted inside of a ceramic package, according to the present invention.

FIG. 14D illustrates a schematic cross-section view of a sixteenth example of a chemiresistor with a recessed, open cavity; mounted inside of a ceramic package, according to the present invention. Chemiresistor 122 is flip-chip mounted to LTCC package 133. Package 133 has an interior ledge with exposed conductors 137, and has an open aperture 135 for providing open access to polymer film 112. Conductive balls 141 interconnect electrodes 143 on substrate 145 to conductors 137 on package 133, in a flip-chip arrangement. A piece of adhesive tape (not shown) can be placed across the open aperture 135 to protect chemically sensitive polymer 112 until use, at which time the tape is removed to expose the active area (i.e., polymer film 112).

Figure 15A:
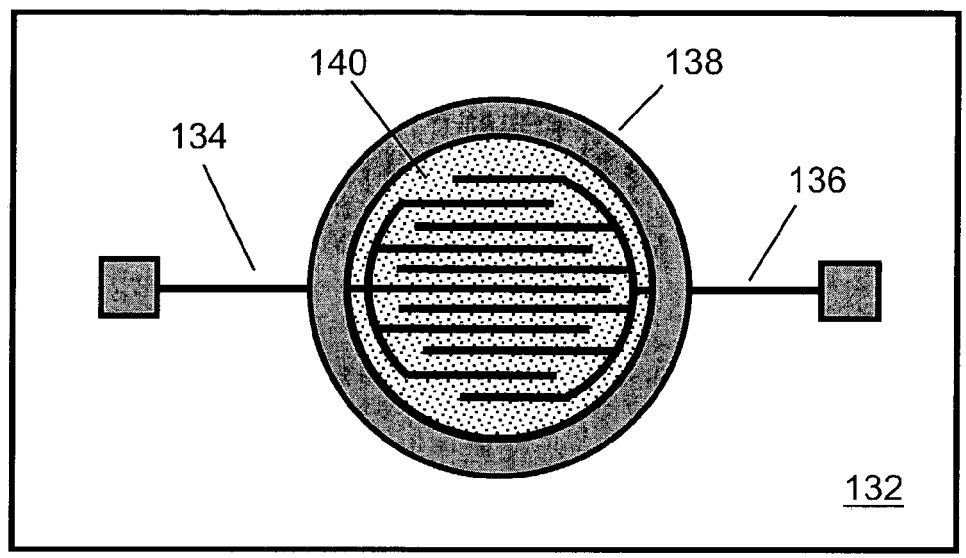
FIG. 15A illustrates a schematic plan view of a seventeenth example of a chemiresistor, according to the present invention.

FIG. 15A illustrates a schematic plan view of a seventeenth example of a chemiresistor, according to the present invention. Electrodes 134 and 136 are arranged a circular, interdigitated array on the surface of substrate 132, and are covered by a chemically sensitive polymer film 140. Seal ring 138 (circular dam, seal ring, confinement ring, gasket, seal) is disposed on the upper surface of substrate 132, which surrounds the circular pattern of interdigitated electrodes 134, 136. Although the use of the word "ring" can convey a circular or oval shape, the shape of seal ring 138 is not limited to being just a circle or oval, it can have other shapes, e.g., square, rectangle, hexagon, polygon, etc. Seal ring 138 may be used to provide confinement of the liquid polymer material after being deposited on substrate 132, while it is drying. Seal ring 138 thereby serves the same function as a recessed, open cavity (as presented earlier), namely, to confine the outer perimeter of polymer film 140 to a defined shape (e.g., circle, square, etc.). Use of this type of "gasket" to confine the liquid chemiresistor ink, instead of a recessed, open cavity, eliminates the need to chemically etch, laser ablate, machine, or otherwise create a recess/cavity into the substrate 132. Seal ring 138 can be made of a polymeric material, epoxy, resin, plastic, polyamide, ceramic, adhesive, rubber, silicone, silastic, wax, or other electrically insulating material. Seal ring 138 can be attached as a pre-formed/pre-fabricated gasket to substrate 132 using a separate adhesive. Alternatively, seal ring 138 can be removable. Alternatively, seal ring 138 can be formed directly by depositing liquid polymer onto substrate 132 in the appropriate shape (circle, square, etc.), and the allowed to dry and harden before depositing-polymer film-140 inside of seal ring 138.

Figure 15B:
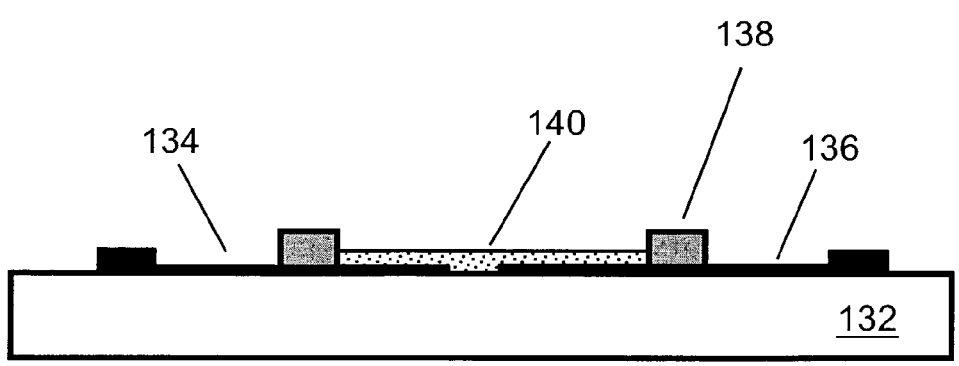
FIG. 15B illustrates a schematic plan view of the seventeenth example of a chemiresistor, according to the present invention.

FIG. 15B illustrates a schematic plan view of the seventeenth example of a chemiresistor, according to the present invention. The cross-section of seal ring 138 is illustrated as a square (or rectangle). Alternatively, the cross-section of seal ring 138 may be a semi-circular or other rounded shape (i.e., without sharp corners), such as might be formed if seal ring 138 was formed directly by pouring or drawing a line of viscous polymeric material that subsequently hardens. A rigid mold may be temporarily used (not shown) to define the shape of seal ring 138 while it hardens. Confinement ring 138 may be removed from substrate 132 after the polymer film 140 has dried and hardened. Alternatively, seal ring 138 may remain in place permanently.

Figure 16:
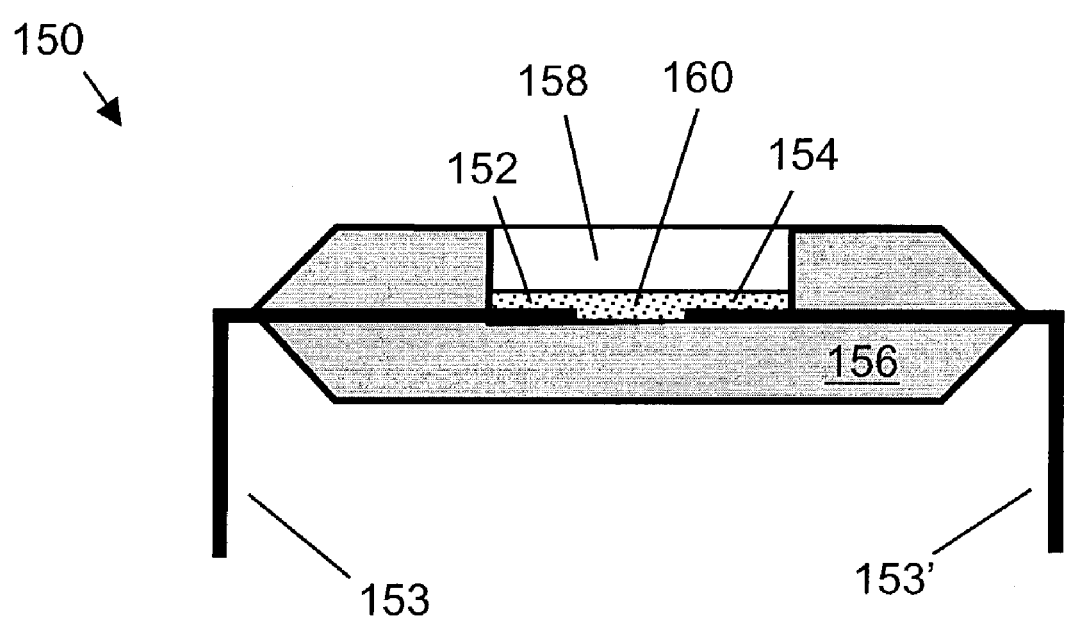
FIG. 16 illustrates a schematic cross section view of the eighteenth example of a chemiresistor, according to the present invention.

FIG. 16 illustrates a schematic cross section view of the eighteenth example of a chemiresistor, according to the present invention. Chemiresistor 150 comprises a plastic molded body 156 (e.g., injection molded) with a pair of external leads 153, 153' that have exposed distal ends 152 and 154, respectively, inside of open volume 158. Chemically sensitive polymer film 160 is disposed on body 156, inside of open volume 158, and contacting electrode ends 152 and 154. Open volume 158 may be created by placing a temporary body/insert inside of volume 158 during plastic molding, which is then removed after molding to leave open volume 158. Alternatively, open volume 158 may be created by mechanically or chemically removing plastic from that space after molding. Conductors 153, 153' may comprise a copper or nickel lead frame. Polymer film 160 may partially fill open volume 158, or substantially fill volume 158.

Figure 17A:
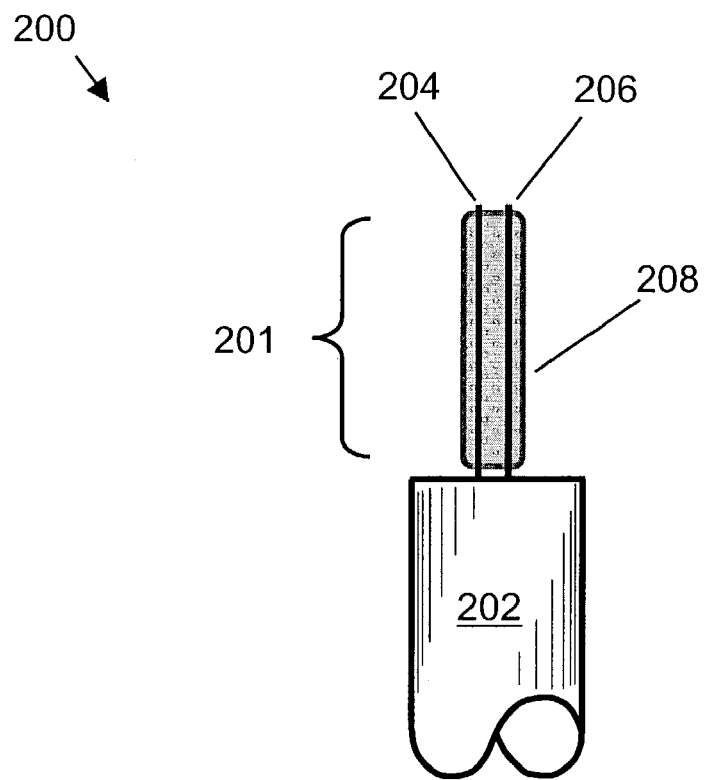
FIG. 17A illustrates a schematic elevation view of a nineteenth example of a chemiresistor, according to the present invention.

FIG. 17A illustrates a schematic elevation view of a nineteenth example of a chemiresistor, according to the present invention. Chemiresistor 200 comprises an electrically insulating support member 202 (e.g., plastic or ceramic rod) supporting a two or more free-standing, exposed, bare conductors 204, 206 (e.g., which can be a pair of wires or pins sticking out of support member 202). The phrase "multi-pin" in this applications refers to the two or more free-standing, exposed, bare conductors 204, 206. The two or more conductors a re oriented substantially parallel to each other and are separated from each other by a small distance. A film of a chemically sensitive polymer 208 is attached to, and suspended in-between, the two or more conductors 204, 206, thereby forming a chemiresistor element 201.

Chemiresistor 200 may be fabricated by dipping the bare conductors 204, 206 into a bath of well-mixed chemiresistor ink and slowly withdrawing it. The ink wicks by capillary action into the small space in-between conductors 204, 206 (i.e., like a soap bubble) and subsequently dries into a free-standing film 208 (supported at two edges by conductors 204, 206). The thickness and shape of the polymer film 208 depends on many factors, including the spacing in-between the two conductors, the wetting characteristics and viscosity of the liquid ink, the cleanliness of the two conductors, etc. This type of design and method of fabrication is not expensive. Also, by not having to use small diameter dispensing tools (e.g., micropipettes, micronozzles), the bath of liquid ink may be continually and easily stirred and mixed (including ultrasonic sonification) to produce a chemiresistor ink with uniform dispersion of carbon particles. Multiple sets of chemiresistors 200 may be simultaneously dipped side-by-side into a bath of chemiresistor ink (i.e., as a batch process), which helps to minimize costs and to control variations between different chemiresistors. This type of design also provides two surfaces of the polymer film 208 that are exposed to the vapor being detected (as opposed to having only one surface exposed in the traditional designs using a flat substrate (see, e.g., FIG. 1A), thereby providing twice the sensitivity as compared to a single-sided film on a flat substrate.

The two or more conductors 204, 206 may be a wire with a circular cross-section, or may have some other shape (square, triangular, crescent, etc.) The gauge of wires 204, 206 may be thinner than 26 gauge. Wires 204, 206 may be made of a high yield strength "spring" copper alloy, such as beryllium-copper (e.g., Cu-2% Be).

The example of a chemiresistor shown in FIG. 17A resembles a standard thermocouple configuration, hence, we have named these types of chemiresistors as a "ChemiCouple™", "ChemiCouple™", and "chemicouple™".

Figure 17B:
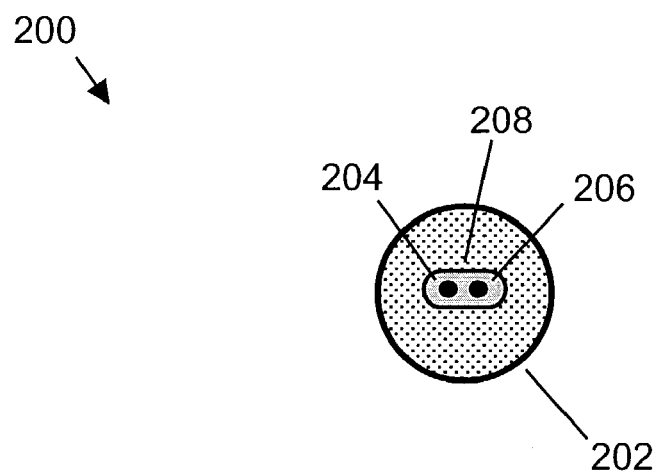
FIG. 17B illustrates a schematic plan view of a nineteenth example of a chemiresistor, according to the present invention.

FIG. 17B illustrates a schematic plan view of the nineteenth example of a chemiresistor, according to the present invention. Polymer film 208 is suspended in-between a pair of bare wires 204 and 206, which are held by support rod 202.

Figure 17C:
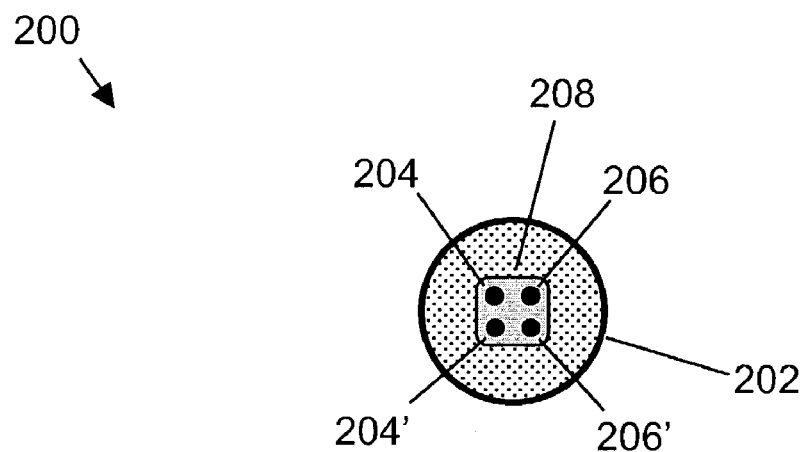
FIG. 17C illustrates a schematic plan view of a twentieth example of a chemiresistor, according to the present invention.

FIG. 17C illustrates a schematic plan view of a twentieth example of a chemiresistor, according to the present invention. Polymer film 208 is suspended in-between four bare wires 204, 204', 206, 206', which are held by support rod 202 and are arranged at the corners of a square. Depending on the wetting characteristics, spacing between wires, etc., polymer film 208 may (or may not) partially or completely fill-in the space inside of the four wires (i.e., in the center of the grouping of wires).

Figure 17D:
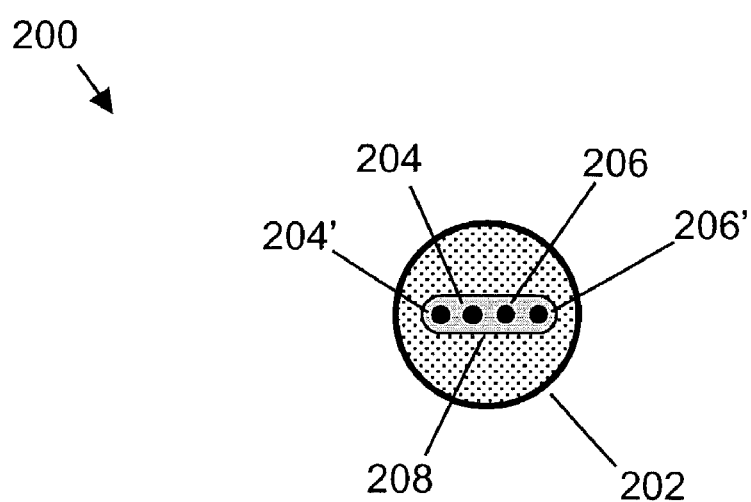
FIG. 17D illustrates a schematic plan view of a twenty-first example of a chemiresistor, according to the present invention.

FIG. 17D illustrates a schematic plan view of a twenty-first example of a chemiresistor, according to the present invention. Polymer film 208 is suspended in-between four bare wires 204, 204', 206 and 206', which are held by support rod 202 and are arranged in a straight line. A four-probe resistance measurement technique can be used with this embodiment (and the one shown in FIG. 17C, as well), since there are four independent conductors/wires covered by the polymer film 208.

Figure 17E:
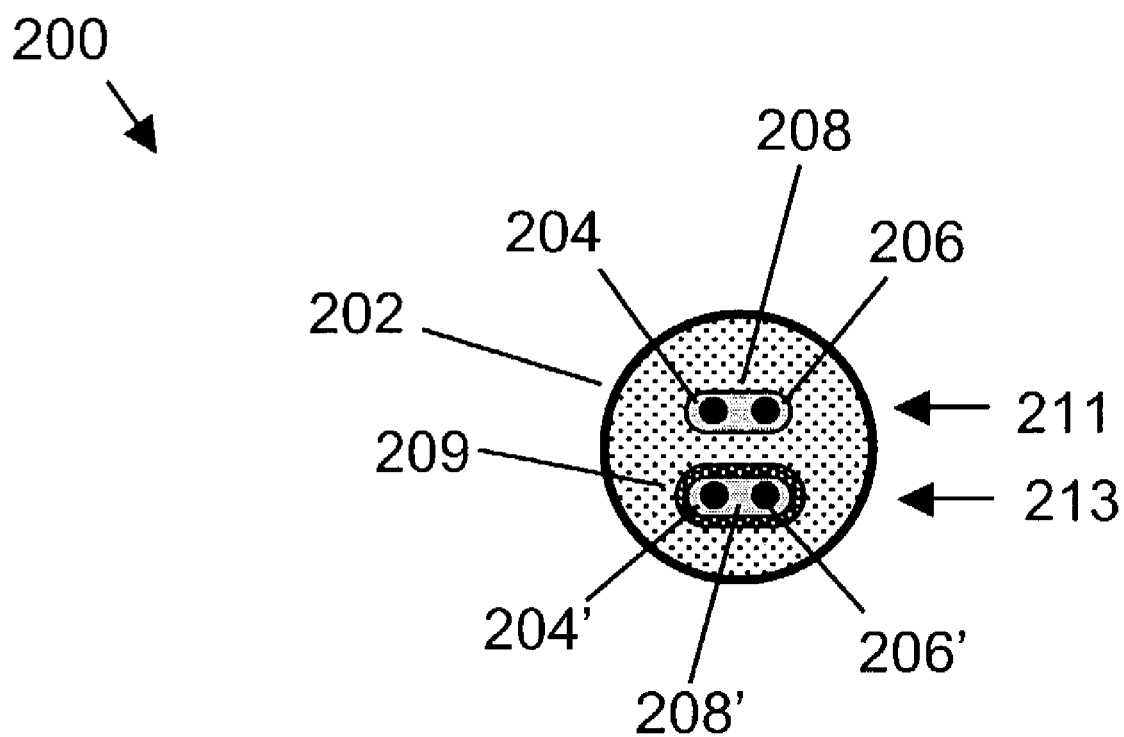
FIG. 17E illustrates a schematic plan view of a twenty-second example of a pair of chemiresistors mounted side-by-side, according to the present invention.

FIG. 17E illustrates a schematic plan view of a twenty-second example of a pair of chemiresistors mounted side-by-side, according to the present invention. First chemiresistor 211 comprises a first polymer film 208 is suspended in-between a first pair of bare wires 204, 206, which are held by support rod 202. Second chemiresistor 213 comprises a second polymer film 208' is suspended in-between a second pair of bare wires 204', 206'. Additionally, a outer coating 209 surrounds and covers the second polymer film 208'. Outer coating 209 may comprise a chemically-selective membrane, such as a proton exchange membrane (e.g., Nafion™). Nafion is an example of a membrane that can allow water vapor/humidity to permeate through the membrane, while blocking most other chemical vapors. This allows the second chemiresistor 213 to act as a reference chemiresistor, since it responds to changes in temperature and/or humidity as the first chemiresistor 211, but not to exposure to the analytes under study (the chemical vapor is blocked by the Nafion covering/coating).

Figure 18A:
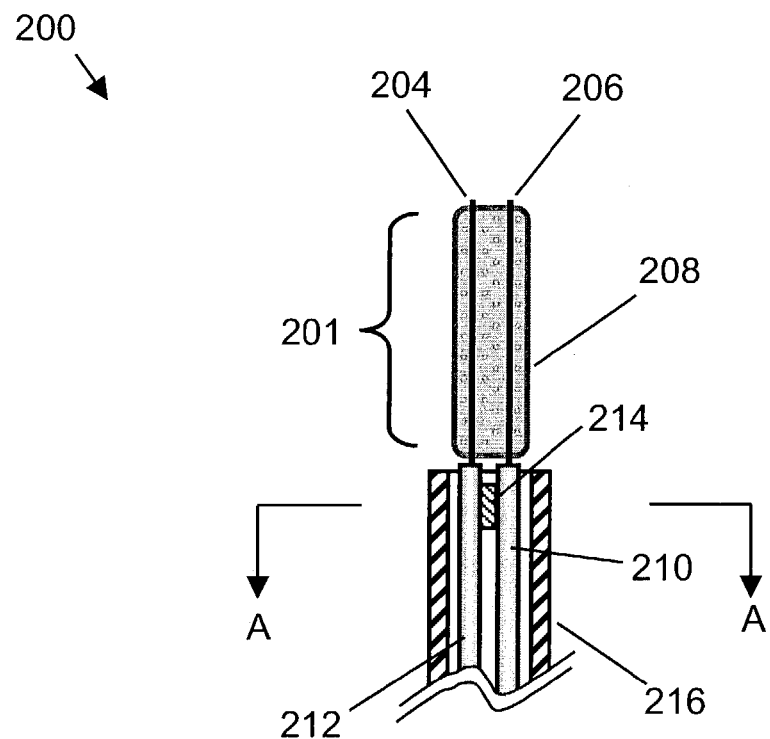
FIG. 18A illustrates a schematic elevation view of a twenty-third example of a chemiresistor, according to the present invention.

FIG. 18A illustrates a schematic elevation view of a twenty-third example of a chemiresistor, according to the present invention. Chemiresistor 200 comprises a bundle of two or more insulated wires, 210 and 212, each wire having a section of exposed conductor 204, 206 (e.g., which can be a pair of wires or pins). The phrase "multi-pin" in this applications refers to the two or more free-standing, exposed, bare conductors 204, 206. The two or more conductors are oriented substantially parallel to each other and are separated from each other by a small distance. A film of a chemically sensitive polymer 208 is attached to, and suspended in-between, the two or more conductors 204, 206, thereby forming a chemiresistor element 201. Spacer 214 may be used to separate insulated wires 210 and 212 apart from each other. A hollow, cylindrical support tube 216 may be used to surround and support the bundle of two or more insulated wires 210,212.

Figure 18B:
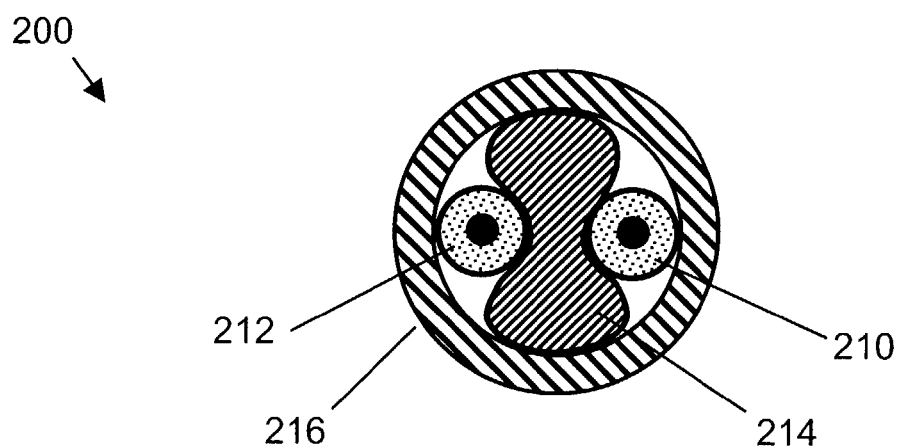
FIG. 18B illustrates a schematic cross-section plan view of the twenty-third example of a chemiresistor, according to the present invention.

FIG. 18B illustrates a schematic cross-section plan view of the twenty-third example of a chemiresistor, according to the present invention.

Figure 18C:
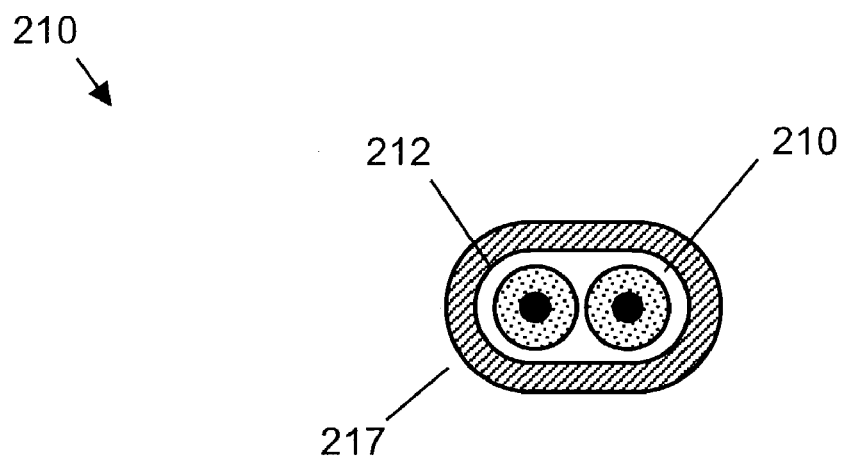
FIG. 18C illustrates a schematic cross-section plan view of a twenty-fourth example of a chemiresistor, according to the present invention.

FIG. 18C illustrates a schematic cross-section plan view of a twenty-fourth example of a chemiresistor, according to the present invention. The pair of insulated wires 210 and 212 are surrounded and supported by a outer layer/sheath of heat-shrinkable plastic tubing 217 that has been heat-shrunk to compress and hold the bundle of wires together.

Figure 19:
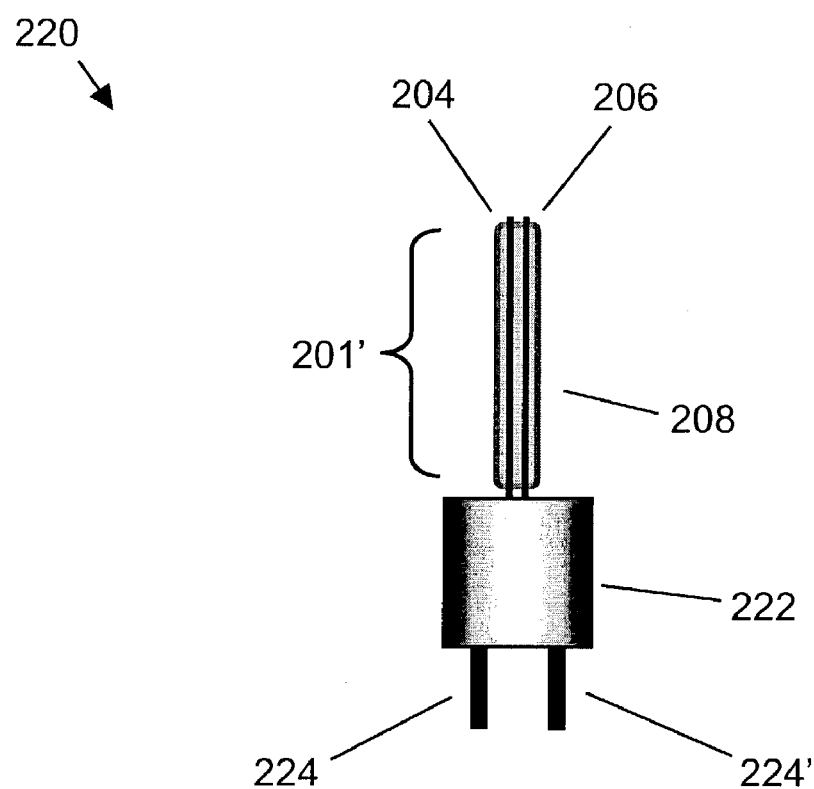
FIG. 19 illustrates a schematic elevation view of a twenty-fifth example of a chemiresistor, according to the present invention.

FIG. 19 illustrates a schematic elevation view of a twenty-fifth example of a chemiresistor, according to the present invention. Chemiresistor element 210 is held and supported by a short, cylindrical plug 222 that has a pair or male electrical connectors 224, 224' extending from the backside of the plug 222 (i.e., in the opposite direction as the chemiresistor element 201). This chemiresistor module 220 (i.e., "chemicouple") can be easily inserted into a female connector (not shown), and easily removed and replaced if damaged or worn-out, etc. In this example, the pair of wires 204, 206 are spaced closer to each other than the example shown in FIG. 17A/B. Here, the aspect ratio (i.e., the length of the wire divided by the spacing between the two wires) is much greater than one (approximately ten).

In some of these embodiments, the spacing between the pair of adjacent wires or conductors may be sufficiently close to allow the chemiresistive ink to wet both wires (due to capillary action) during fabrication, and subsequently form a free-standing film or membrane suspended in-between the two wires. Alternatively, the spacing between wires may be less than 1 mm. Alternatively, the spacing between wires may be less than about 100 microns. Alternatively, the spacing between wires may be greater than about 50 microns and less than about 100 microns. Alternatively, the aspect ratio (i.e., the length of the wire divided by the spacing between the two wires) may be greater than five. Alternatively, the aspect ratio (i.e., the length of the wire divided by the spacing between the two wires) may be greater than ten.

Figure 20:
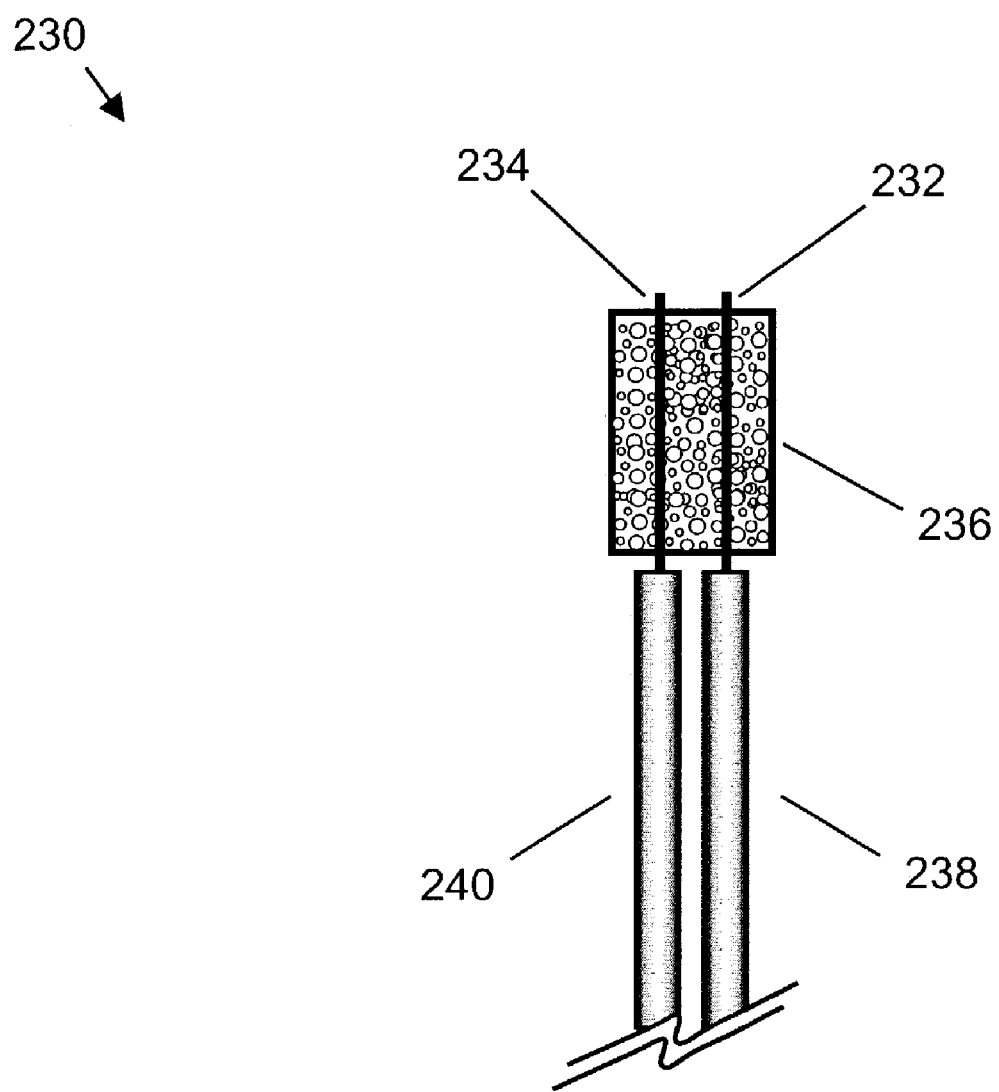
FIG. 20 illustrates a schematic elevation view of a twenty-sixth example of a chemiresistor, according to the present invention.

FIG. 20 illustrates a schematic elevation view of a twenty-sixth example of a chemiresistor, according to the present invention. Chemiresistor 230 comprises a pair of insulated wires 238, 240 with exposed, bare ends 232, 234, which have been inserted into a block (cube, cylinder, etc.) of a porous material 236. The chemiresistor ink has been wicked up into the porous/sponge material 236 and allowed to dry thereby depositing the chemically sensitive polymer inside of the porous block 236, which is in contact with the two bare electrodes 232, 234.

Figure 21A:
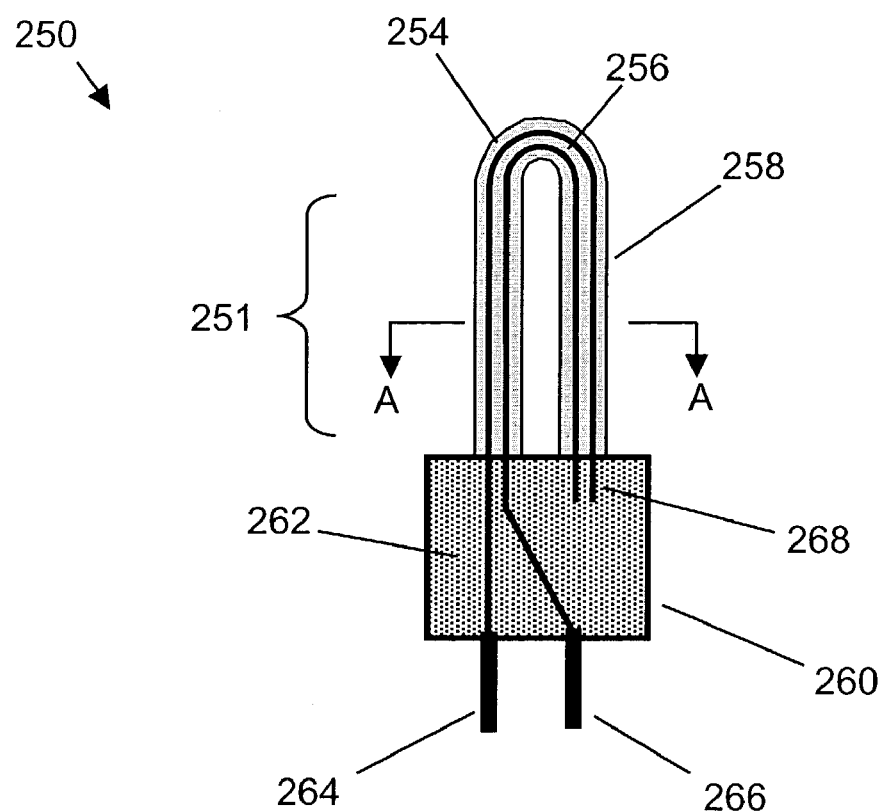
FIG. 21A illustrates a schematic elevation view of a twenty-seventh example of a chemiresistor, according to the present invention.

FIG. 21A illustrates a schematic elevation view of a twenty-seventh example of a chemiresistor, according to the present invention. Chemiresistor 250 comprises an electrically insulating base 260, which support a pair of U-shaped wires 254 and 256. Chemically sensitive polymer 258 covers and contacts the pair of U-shaped wires 254 and 256. The distal ends of wires 254 and 256 are embedded into base 260; this provides greater structural support and rigidity than the embodiment of, for example, FIG. 17A that has two wires 204, 206 that are unsupported at their distal ends. This type of folded geometry (i.e., the U-shaped wires) provides a more compact geometry than a pair of linear wires (as in FIG. 17A).

Figure 21B:
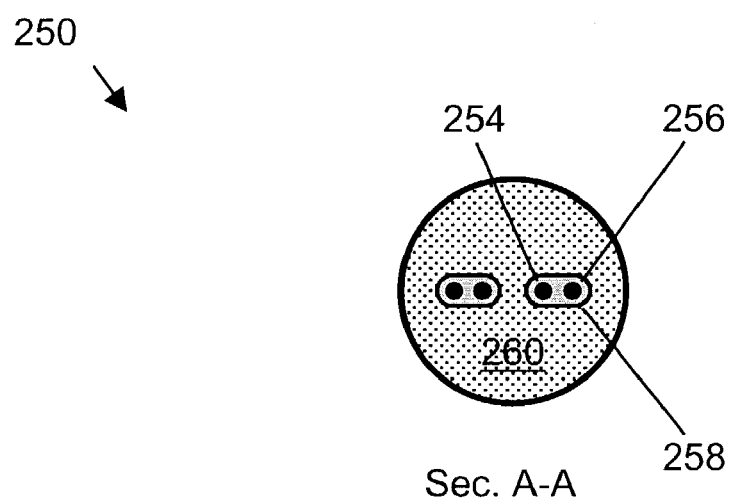
FIG. 21B illustrates a schematic plan view through cross-section A—A of the twenty-seventh example of a chemiresistor, according to the present invention.

FIG. 21B illustrates a schematic plan view through cross-section A—A of the twenty-seventh example of a chemiresistor, according to the present invention.

Figure 22A:
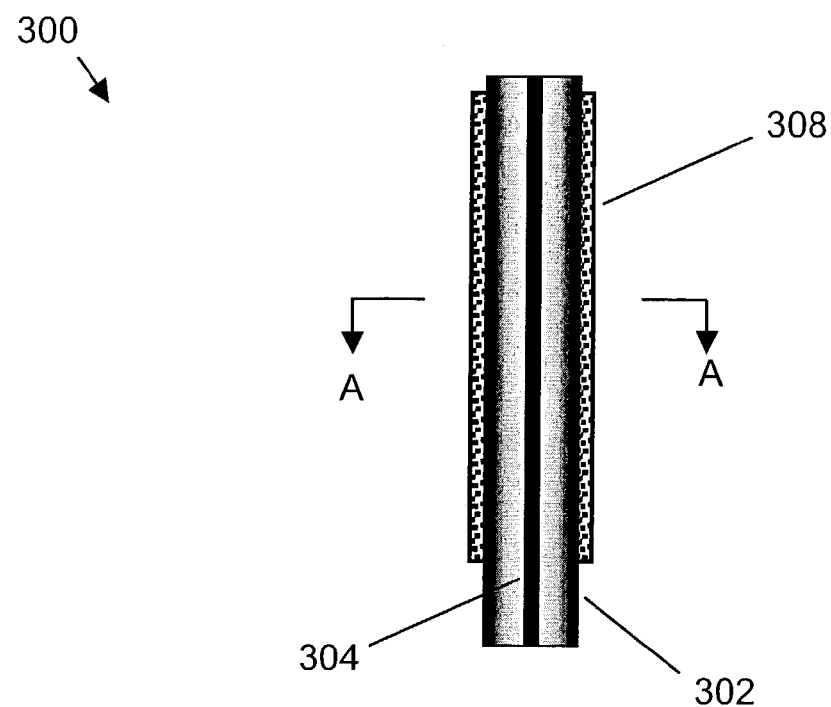
FIG. 22A illustrates a schematic elevation view of a twenty-eighth example of a chemiresistor, according to the present invention.

FIG. 22A illustrates a schematic elevation view of a twenty-eighth example of a chemiresistor, according to the present invention. Chemiresistor 300 comprises a rod 302 made of an electrically insulating material. Rod 302 may have a cylindrical, square, or rectangular cross section. The aspect ratio of rod 302 may be greater than about five. Two or more conductors 304 (only one is illustrated in this elevation view) are disposed on the outer surface of rod 302. In this embodiment, conductors 304 are oriented parallel to the long direction of rod 302. Chemically sensitive polymer 308 covers and contacts both rod 302 and conductors 304. Polymer 308 may be applied by dipping rod 302 and conductors 304 into a bath of well-mixed chemiresistor ink. Multiple "dips" may be performed, each time allowing the wet film to dry before dipping again, to build up a uniform, thick coating (if desired). Conductors 304 may be a thin film or thick film of a conducting metal, deposited using well-known techniques in the microelectronics industry (e.g., sputtering, evaporation, CVD, PVD, PACVD, screen printing, etc., with or without a mask and photoimagable coatings).

Figure 22B:
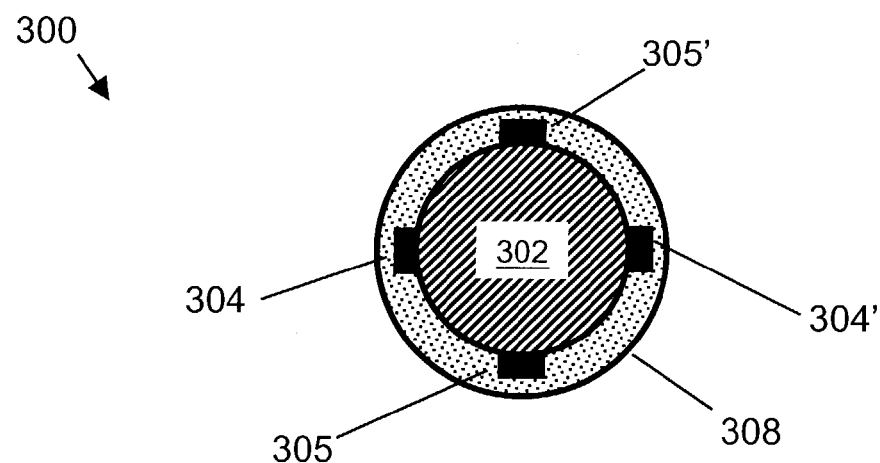
FIG. 22B illustrates a schematic plan view through cross-section A—A of the twenty-eighth example of a chemiresistor, according to the present invention.

FIG. 22B illustrates a schematic plan view through cross-section A—A of the twenty-eighth example of a chemiresistor, according to the present invention. Rod 302 may have a cylindrical cross-section and have a solid core. The four conductors 304, 304', 305, 305' have been evenly placed around the circumference of rod 302. Many different options exist for measuring the resistance of polymer film 308. The resistance across electrodes 304 and 305 may be measured. Alternatively, the resistance across electrodes 304 and 304' may be measured. Alternatively, electrodes 304 and 305 may be connected together, and electrodes 304' and 305' may be connected, and the resistance measured across these two pairs of connected electrodes. Other permeations may be used, as well, including measuring different combinations of electrodes in the same chemiresistor.

Figure 22C:
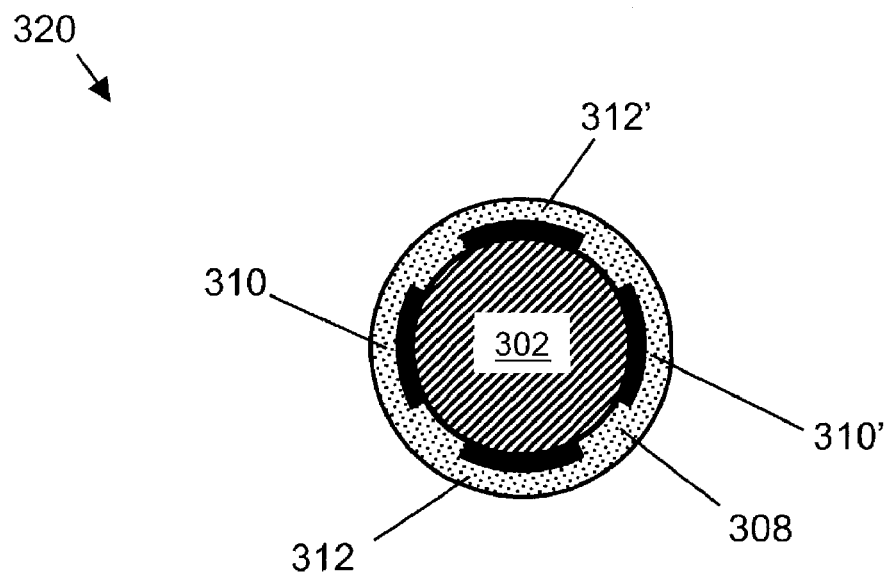
FIG. 22C illustrates a schematic plan view through cross-section A—A of another version of the twenty-eighth example of a chemiresistor, according to the present invention.

FIG. 22C illustrates a schematic plan view through cross-section A—A of another version of the twenty-eighth example of a chemiresistor, according to the present invention. In this version, the four electrodes 320, 310', 312, 312' have a greater circumferential width or extent than those shown in FIG. 22B. The wider electrodes in this version provides greater contact area with the overlying polymer film 308.

Figure 23:
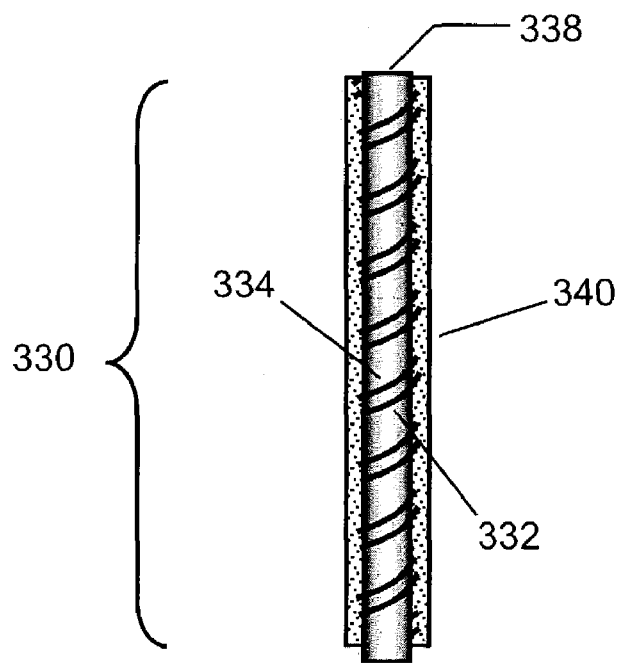
FIG. 23 illustrates a schematic elevation view of a twenty-ninth example of a chemiresistor, according to the present invention.

FIG. 23 illustrates a schematic elevation view of a twenty-ninth example of a chemiresistor, according to the present invention. Chemiresistor 330 comprises a cylindrical rod 338 made of an electrically insulating material. Two conductors 332, 334 wrap around the outer surface of rod 338 in a dual-track, spiral wrapped geometry. Chemically sensitive polymer 340 covers and contacts the pair of conductors 332, 334. Use of a spiral wrapped pattern in this embodiment provides a greater contact area of the conductors 332, 334 with the polymer film 340 than straight, linear designs, as shown in FIGS. 22A and 22B, for example. This concept of having an electrode layout that maximizes the contact area is similar to the use of a dual-track concentric spiral pattern on a flat substrate, as was presented earlier (e.g., see FIG. 4A).

In other embodiments of the present invention, the electrically insulating support member (which is shown as a cylindrical rod 302 in FIGS. 22A, 22B, 22C and as cylindrical rod 338 in FIG. 23), may have a shape other than a cylindrical rod, for example, a square or rectangular cross-section. Other terms for the support member in these figures include "stick" and "dip-stick". Use of the term "dip-stick" connotes a dip-stick in an automobile, where the member is long and slender, with a rectangular cross-section, and where the member is dipped into a fluid (oil, hydraulic fluid) that sticks to the member due to surface tension and viscosity. In this sense, these chemiresistor elements are like sticks or dip-sticks because they are generally long and thin (i.e., slender), and may be dipped into a bath of well-mixed chemiresistor ink that subsequently sticks to the stick when withdrawn.

Figure 24A:
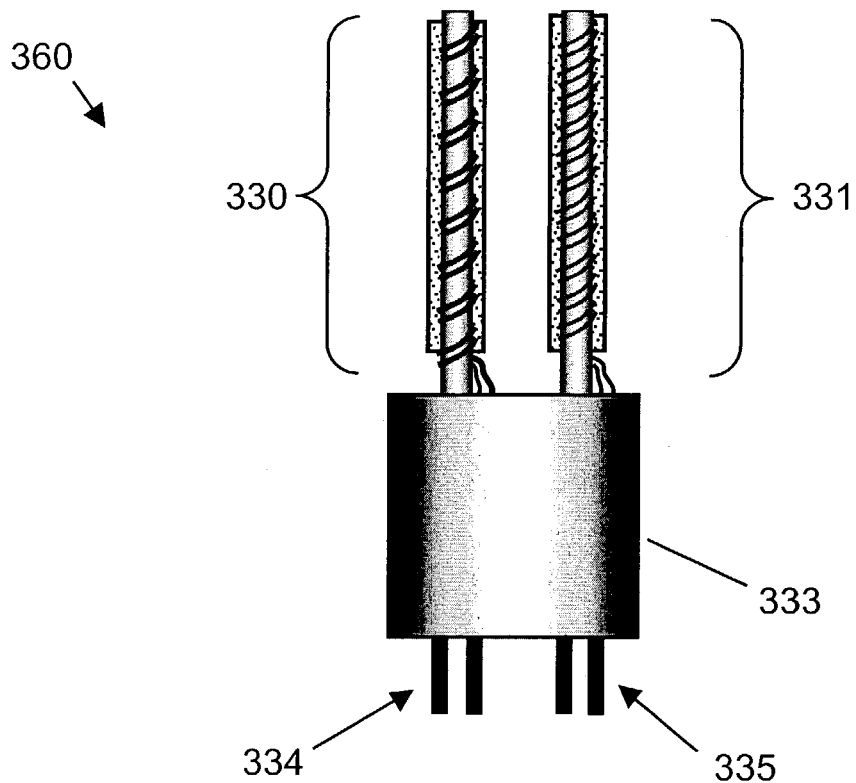
FIG. 24A illustrates a schematic elevation view of a thirtieth example of a chemiresistor, according to the present invention.

FIG. 24A illustrates a schematic elevation view of a thirtieth example of a chemiresistor, according to the present invention. Chemiresistor 360 comprises a cylindrical plug 333 made of an electrically insulating material. Two spiral-wrapped chemiresistor elements 330 and 331 are supported by plug 333, and extend outwards from the upper surface of plug 333. The chemically sensitive polymer film used on elements 330 and 331 may be the same or different. If the chemically sensitive polymer film used on elements 330 and 331 is the same, then an optional covering of Nafion™ or other chemically-selective membrane (not shown) may be used to cover the chemically sensitive polymer of one of the elements, thereby making it into a reference electrode/element. A pair of male electrical connectors 334 and 335 (e.g., pins) extend from the lower surface of plug 333 and are electrically connected to the pair of conductors on each element 330 and 331, respectively. Note that the diameter of wires on element 331 is smaller than on element 330, and that the pitch of wires on element 331 is greater (i.e., more turns per inch) than on element 330; and both factors will affect the baseline resistance.

Figure 24B:
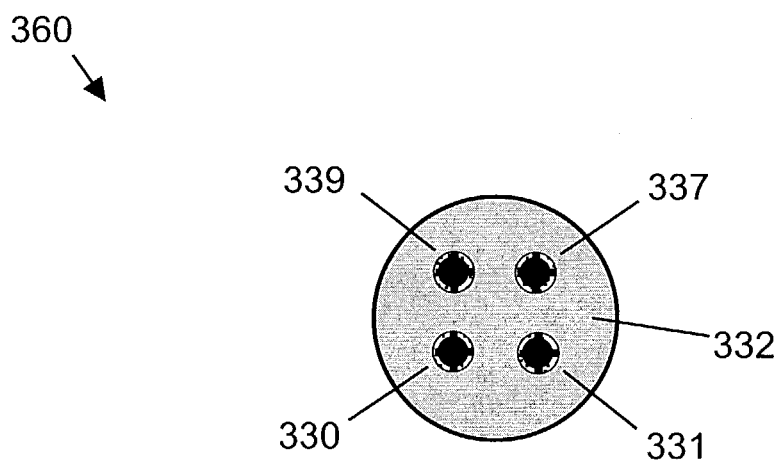
FIG. 24B illustrates a schematic plan view of the thirtieth example of a chemiresistor, according to the present invention.

FIG. 24B illustrates a schematic plan view of the thirtieth example of a chemiresistor, according to the present invention. In this embodiment, four spiral-wrapped chemiresistor elements 330, 331, 337, and 339 are supported by plug 333 (with a corresponding number of male electrical pins on the bottom face of plug 333). The chemically sensitive polymer film on each chemiresistor element 330, 331, 337, and 339 may be the same or different. If different, the four different polymer hosts may be selected from the group listed in Table 1.

In FIGS. 24A and 24B, each chemiresistor element (e.g., 330, 331) may be permanently attached to plug 333, or removably attached to plug 333 to provide quick and easy replacement of a damaged chemiresistor element. If removable, spring-loaded electrical contacts internal to plug 333 may be used to provide a secure and reliable electrical connection to the pair or conductors on each element.

Other embodiments of the present invention comprise a method of fabricating a chemiresistor. In one embodiment, the method comprises (with reference, for example, to FIG. 17A):

a) providing an electrically insulating support member 202 comprising two or more free-standing bare conductors 204, 206 supported at one end by the support member 202, wherein the conductors 204, 206 are oriented substantially parallel to each other, and are separated from each other by a small distance;

b) dipping the exposed ends of the two or more free-standing bare conductors 204, 206 into a bath comprising the chemically sensitive polymer mixed with a solvent; whereby the chemically sensitive polymer wicks in-between the two or more free-standing bare conductors;

c) removing the wetted conductors from the bath; and d) removing the solvent by evaporation, whereby a solid film of chemically sensitive polymer 208 remains attached to, and suspended in-between, the two or more free-standing bare conductors 204, 206.

The particular examples discussed above are cited to illustrate particular embodiments of the invention. Other applications and embodiments of the apparatus and method of the present invention will become evident to those skilled in the art. For example, a protective screen or mesh (not shown) may be used to cover and protect the free-standing polymer film 208 that is attached to, and suspended in-between, the two or more free-standing bare conductors 204, 206 in FIG. 17A.

The actual scope of the invention is defined by the claims appended hereto.

What is claimed is:

1. A circular chemiresistor, comprising:
an electrically insulating substrate comprising a pair of conductive lines arranged in a dual-track, circle-filling geometry; and
a chemically-sensitive polymer contacting said pair of conductive lines.

2. The circular chemiresistor of claim 1, wherein the circle-filling geometry comprises a concentric spiral pattern.

3. The circular chemiresistor of claim 2, wherein the spacing between said pair of conductive lines is uniform.

4. The circular chemiresistor of claim 3, wherein the spacing between the outside edges of said pair of conductive lines is less than or equal to approximately fifty microns.

5. The circular chemiresistor of claim 2, wherein the outside diameter of the concentric spiral pattern is less than or equal to approximately one millimeter.

6. The circular chemiresistor of claim 2, wherein the concentric spiral pattern comprises two or three turns.

7. The circular chemiresistor of claim 2, wherein the width of each conductive line is less than or equal to approximately fifty microns.

8. The circular chemiresistor of claim 1, wherein the chemically-sensitive polymer comprises a material that swells when exposed to vapors of a volatile compound.

9. The circular chemiresistor of claim 8, wherein the chemically-sensitive polymer comprises conductive particles embedded in a polymer matrix selected from the group consisting of poly(n-vinyl pyrrolidone), poly(vinyl alcohol), poly(ethylene-vinyl acetate), poly(isobutylene), poly(n-vinyl pyrrolidone), poly(epichlorohydrin), ethyl cellulose, poly(chloroprene), poly(diphenoxyphosphazine, and poly(caprolactone).

10. The circular chemiresistor of claim 1, wherein the substrate has a rectangular shape, with outside dimensions less than or equal to approximately 3 mm by 7 mm.

11. The circular chemiresistor of claim 1, wherein said pair of conductive lines comprise a plurality of interdigitated electrodes constrained to fit inside of a circle.

12. The circular chemiresistor of claim 1, further comprising a coating of a chemically-selective material that surrounds and covers said chemically-sensitive polymer.

13. The circular chemiresistor of claim 12, wherein the chemically-selective material comprises a material that allows water vapor to permeate through, while blocking other chemical vapors.

14. The circular chemiresistor of claim 13, wherein the chemically-selective material comprises Nafion.

15. A circular chemiresistor, comprising;
an electrically insulating substrate comprising a recessed, open circular cavity and a pair of conductive lines, each line having a distal end disposed inside of the recessed, open circular cavity; and
a chemically-sensitive polymer confined within the recessed, open circular cavity, contacting said pair of conductive lines;
wherein said pair of conductive lines are arranged in a dual-track, concentric spiral pattern that is confined within the recessed, open circular cavity.

16. The circular chemiresistor of claim 15, wherein the chemically-sensitive polymer comprises a material whose electrical resistance changes when exposed to vapors of a volatile compound, selected from the group consisting of poly(n-vinyl pyrrolidone), poly(vinyl alcohol), poly(ethylene-vinyl acetate), poly(isobutylene), poly(n-vinyl pyrrolidone), poly(epichlorohydrin), ethyl cellulose, poly(chloroprene), poly(diphenoxyphosphazine, and poly(caprolactone).

17. The circular chemiresistor of claim 15, wherein the spacing between the outside edges of said lines is uniform.

18. The circular chemiresistor of claim 15, wherein the spacing between the outside edges of said pair of conductive lines is less than or equal to approximately fifty microns.

19. The circular chemiresistor of claim 15, wherein the outside diameter of the concentric spiral pattern is less than or equal to approximately one millimeter.

20. The circular chemiresistor of claim 15, wherein the concentric spiral pattern comprises two or three turns.

21. The circular chemiresistor of claim 15, wherein the width of each conductive line is less than or equal to approximately fifty microns.

22. The circular chemiresistor of claim 15, wherein said pair of conductive lines comprise a plurality of interdigitated electrodes constrained to fit inside of a circle.

23. The chemiresistor of claim 15, wherein the substrate comprises one or more multilayered materials selected from the group consisting of printed wiring board materials LTCC, and HTCC.

* * * * *